US012447268B2

(12) United States Patent
Grant et al.

(10) Patent No.: US 12,447,268 B2
(45) Date of Patent: Oct. 21, 2025

(54) INFUSION PUMP ASSEMBLY

(71) Applicant: DEKA Products Limited Partnership, Manchester, NH (US)

(72) Inventors: Kevin L. Grant, Litchfield, NH (US); Brian D. Tracey, Litchfield, NH (US); Patrick Poisson, Silver Spring, MD (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 292 days.

(21) Appl. No.: 16/216,392

(22) Filed: Dec. 11, 2018

(65) Prior Publication Data

US 2019/0351133 A1 Nov. 21, 2019

Related U.S. Application Data

(60) Provisional application No. 62/597,246, filed on Dec. 11, 2017.

(51) Int. Cl.

| | |
|---|---|
| ***A61M 5/145*** | (2006.01) |
| ***A61M 5/142*** | (2006.01) |
| ***A61M 5/168*** | (2006.01) |

(52) U.S. Cl.

CPC ........ *A61M 5/14244* (2013.01); *A61M 5/145* (2013.01); *A61M 5/168* (2013.01); *A61M 2205/3569* (2013.01)

(58) Field of Classification Search

CPC .......... A61M 5/14244; A61M 5/14248; A61M 5/1413; A61M 5/162; A61M 5/1456; A61M 5/282; A61M 2005/14268; B65D 83/00; A61J 1/2031

See application file for complete search history.

(56) References Cited

U.S. PATENT DOCUMENTS

| | | | |
|---|---|---|---|
| 7,306,578 | B2 | 12/2007 | Gray et al. |
| 8,262,616 | B2 | 9/2012 | Grant et al. |
| 8,414,522 | B2 | 4/2013 | Kamen et al. |
| 8,491,570 | B2 | 7/2013 | Kamen et al. |

(Continued)

FOREIGN PATENT DOCUMENTS

| | | | |
|---|---|---|---|
| CN | 106029122 | A | 10/2016 |
| EP | 1646412 | A0 | 4/2006 |

(Continued)

OTHER PUBLICATIONS

International Search Report and Written Opinion for corresponding PCT Application No. PCT/US2018/064960 dated Jun. 5, 2019.

(Continued)

*Primary Examiner* — Laura A Bouchelle
*Assistant Examiner* — Anna E Goldberg-Richmeier
(74) *Attorney, Agent, or Firm* — McCormick, Paulding & Huber PLLC

(57) ABSTRACT

A disposable housing assembly. The disposable housing assembly includes a reservoir cavity, a needle located within the reservoir cavity, a fluid path fluidly connected to the needle, and a cover, wherein the cover is in a first position, the reservoir cavity and needle are exposed and when the cover is in a second position, the reservoir and needle are not exposed.

39 Claims, 75 Drawing Sheets

(56) References Cited

U.S. PATENT DOCUMENTS

| | | | | |
|---|---|---|---|---|
| 8,684,968 | B2 * | 4/2014 | Genosar | A61M 5/282 604/132 |
| 2008/0269713 | A1 | 10/2008 | Kavazov | |
| 2013/0110053 | A1 * | 5/2013 | Yoshino | A61J 1/1406 604/201 |
| 2014/0107579 | A1 | 4/2014 | Lanigan et al. | |
| 2015/0174320 | A1 * | 6/2015 | Grant | A61M 5/14244 604/535 |
| 2016/0256352 | A1 * | 9/2016 | Bar-El | A61M 5/1456 |
| 2016/0317737 | A1 * | 11/2016 | Schabbach | A61M 5/14232 |
| 2021/0128823 | A1 * | 5/2021 | Shaked | A61M 5/158 |

FOREIGN PATENT DOCUMENTS

| | | | | |
|---|---|---|---|---|
| JP | 2010179108 | A | 8/2010 | |
| WO | 2011156373 | A1 | 12/2011 | |
| WO | 2012002190 | A1 | 1/2012 | |
| WO | WO-2012032411 | A2 * | 3/2012 | A61M 5/14244 |
| WO | 2015003141 | A1 | 1/2015 | |
| WO | 2015091760 | A1 | 6/2015 | |
| WO | 2016154413 | A1 | 9/2016 | |

OTHER PUBLICATIONS

Japanese Office Action and its English translation for corresponding Japanese Application No. 2020-531940 dated Aug. 22, 2022.

* cited by examiner

SECTION B-B
SCALE 1:1

SECTION A-A
SCALE 1:1

SECTION B-B
SCALE 1:1

SECTION A-A
SCALE 1:1

INFUSION PUMP ASSEMBLY

CROSS REFERENCE TO RELATED APPLICATION(S)

The present application is a Non-provisional Application which claims the benefit of priority to U.S. Provisional Patent Application No. 62/597,246 filed Dec. 11, 2017 which is hereby incorporated herein by reference in its entirety.

FIELD OF THE INVENTION

This application relates generally to fluid delivery systems, and more particularly to infusion pump assemblies.

BACKGROUND

Many potentially valuable medicines or compounds, including biologics, are not orally active due to poor absorption, hepatic metabolism or other pharmacokinetic factors. Additionally, some therapeutic compounds, although they can be orally absorbed, are dosed with a frequency making it difficult or impossible for a patient to maintain the desired schedule using an oral formulation. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight, and cost of these devices is also an ongoing challenge. Additionally, these devices often apply to the skin and pose the challenge of frequent re-location for application.

SUMMARY OF THE INVENTION

In accordance with first implementation, a disposable housing assembly is disclosed. The disposable housing assembly including a reservoir cavity; a needle located within the reservoir cavity; a fluid path fluidly connected to the needle; and a cover, wherein the cover is in a first position, the reservoir cavity and needle are exposed and when the cover is in a second position, the reservoir and needle are not exposed.

Some embodiments of this implementation of the invention include one or more of the following. Wherein the needle comprises a first end and a second end, the first end inside a gasket and the second end inside an overmolded portion needle cover. A rigid portion needle cover. Wherein the needle comprises a first end and a second end, wherein the first end is exposed to the reservoir cavity and the second end is exposed to the fluid path. A cylindrical guide located about the gasket. Wherein the needle comprises a bend. A gasket, wherein the needle is located in the gasket. An exit fluidly connected to the fluid path. A hinging door, wherein the hinging door comprises at least one catch feature. At least one seal located about the needle. Wherein the hinging door comprises at least one car configured to assist with pulling a reservoir towards the reservoir cavity. Wherein the hinging door comprising at least one catch feature. Wherein the reservoir cavity comprises: a barrier layer; and a fluid, wherein the fluid is maintained between the reservoir cavity and the barrier layer. A predetermined length of tubing attached to the exit. A luer of an infusion set attached to the tubing. A cannula attached to the luer. Wherein the cover comprises at least one catch feature. Wherein the cover comprises a plurality of catch features. Wherein the cover moves vertically from a first position to a second position. Wherein the cover moves horizontally from a first position to a second position. Wherein the cover comprises a needle holder feature. Wherein the cover comprising a support feature. Wherein the needle comprises a first end and a second end, the first end attached to a gasket.

In accordance with first implementation, a blowmolded reservoir is disclosed. The blowmolded reservoir comprising: a first section; a port section comprising: an opening; and at least one leg, wherein the port section is fluidly connected to the first section; and a tail section.

Some embodiments of this implementation of the invention include one or more of the following. Wherein the tail section is sealed off from the first section and the port section. Wherein the first section is a domed section. Wherein the first section is an accordion shape. Wherein the first section is collapsible. Wherein the port section comprises a septum. Wherein the port section comprises a gasket. Wherein the portion section comprises a needle.

In accordance with first implementation, a blowmolded reservoir is disclosed. The blowmolded reservoir comprising: a first section; a port section comprising: an opening; and at least one leg, wherein the port section is fluidly connected to the first section; a tail section; and a sacrificial neck section.

Some embodiments of this implementation of the invention include one or more of the following. Wherein the tail section is sealed off from the first section and the port section. Wherein the first section is a domed section. Wherein the first section is an accordion shape. Wherein the first section is collapsible. Wherein the port section comprises a septum. Wherein the port section comprises a gasket. Wherein the port section comprises a needle.

In accordance with first implementation, a blowmolded reservoir is disclosed. The blowmolded reservoir comprising: a first section; and a port section comprising: an opening; and at least one leg, wherein the port section is fluidly connected to the first section.

Some embodiments of this implementation of the invention include one or more of the following. Wherein the first section is a domed section. Wherein the first section is an accordion shape. Wherein the first section is collapsible. Wherein the port section comprises a septum. Wherein the port section comprises a gasket. Wherein the portion section comprising a needle.

In accordance with first implementation, a disposable housing assembly is disclosed. The disposable housing assembly comprising: a reservoir cavity; a needle located within the reservoir cavity; a fluid path fluidly connected to the needle; and a hinging door, wherein when the hinging door is in a first open position, the reservoir cavity and needle are exposed and when the hinging door is in a second closed position, the reservoir and needle are not exposed.

Some embodiments of this implementation of the invention include one or more of the following. A gasket, wherein the needle is located in the gasket. An exit fluidly connected to the fluid path. Wherein the hinging door comprising at least one catch feature. At least one seal located about the needle. Wherein the hinging door comprises at least one ear configured to assist with pulling a reservoir towards the reservoir cavity. Wherein the hinging door comprises at least one catch feature. Wherein the reservoir cavity comprises: a barrier layer; and a fluid, wherein the fluid is maintained between the reservoir cavity and the barrier layer. A predetermined length of tubing attached to the exit. A luer of an infusion set attached to the tubing. A cannula attached to the luer.

In accordance with first implementation, a disposable housing assembly is disclosed. The disposable housing assembly comprising: a reservoir cavity; a needle located within the reservoir cavity; a fluid path fluidly connected to the needle; and a hinging door, wherein when the hinging door is in a first open position, the reservoir cavity and needle are exposed and when the hinging door is in a second closed position, the reservoir and needle are not exposed.

Some embodiments of this implementation of the invention include one or more of the following. Wherein the disposable housing assembly further including a latch. Further including a gasket, wherein the needle is located in the gasket. Further including an exit fluidly connected to the fluid path. Wherein the hinging door comprises at least one catch feature. Further including at least one seal located about the needle. Wherein the hinging door comprises at least one car configured to assist with pulling a reservoir towards the reservoir cavity. Wherein the hinging door comprises at least one catch feature. Wherein the reservoir cavity comprises: a barrier layer; and a fluid, wherein the fluid is maintained between the reservoir cavity and the barrier layer. Further including a predetermined length of tubing attached to the exit. Further including a luer of an infusion set attached to the tubing. Further including a cannula attached to the luer.

In accordance with first implementation, a reservoir system is disclosed. The reservoir system comprising: a blowmolded reservoir; and a disposable housing assembly comprising: a reservoir cavity; a fluid path; a cover for the reservoir cavity a needle; wherein moving the cover from a first position to a second position creates a fluid connection between the needle and the blowmolded reservoir and primes the fluid path.

Some embodiments of this implementation of the invention include one or more of the following. A gasket, wherein the needle is located in the gasket. Wherein the cover is hingeably attached to the disposable housing assembly. Wherein the cover can be positioned in a first open position and a second closed position. Wherein the cover moves from the first open position to the second closed position. Wherein the cover is prevented from moving from the second closed position to the first open position. Wherein the cover moving from the first open position to the second closed position acts to prime the disposable housing assembly. Wherein the disposable housing assembly further comprises an exit fluidly connected to the fluid path. A predetermined length of tubing attached to the exit. A luer of an infusion set attached to the tubing. A cannula attached to the luer. Wherein the blowmolded reservoir comprising: a first section; and a port section comprising: an opening; at least one leg, wherein the port section is fluidly connected to the first section. Wherein the first section is a domed section. Wherein the first section is collapsible. Wherein the port section comprises a septum. Wherein the port section comprises a gasket. Wherein the port section comprises a needle. Wherein the reservoir cavity comprises: a barrier layer; and a fluid, wherein the fluid is maintained between the reservoir cavity and the barrier layer. Wherein the first section is an accordion shape.

In accordance with first implementation, a blowmolded reservoir is disclosed. The blowmolded reservoir comprising: a first section; a port section comprising: an opening; at least one leg, wherein the port section is fluidly connected to the first section; and a tail section.

Some embodiments of this implementation of the invention include one or more of the following. Wherein the tail section is sealed off from the first section and the port section. Wherein the first section is a domed section. Wherein the first section is an accordion shape. Wherein the first section is collapsible. Wherein the port section comprises a septum. Wherein the port section comprises a gasket. Wherein the port section comprises a needle.

In accordance with first implementation, a blowmolded reservoir is disclosed. The blowmolded reservoir comprising: a first section; a port section comprising: an opening; at least one leg, wherein the port section is fluidly connected to the first section; a tail section; and a sacrificial neck section.

Some embodiments of this implementation of the invention include one or more of the following. Wherein the tail section is sealed off from the first section and the port section. Wherein the first section is a domed section. Wherein the first section is an accordion shape. Wherein the first section is collapsible. Wherein the port section comprises a septum. Wherein the port section comprises a gasket. Wherein the port section comprises a needle.

The details of one or more embodiments are set forth in the accompanying drawings and the description below. Other features and advantages will become apparent from the description, the drawings, and the claims.

BRIEF DESCRIPTION OF THE DRAWINGS

FIGS. 1A-2B are various views of one embodiment of a disposable housing assembly;

FIGS. 2A-2J are various views of one embodiment of a disposable housing assembly;

and

Figure 18:
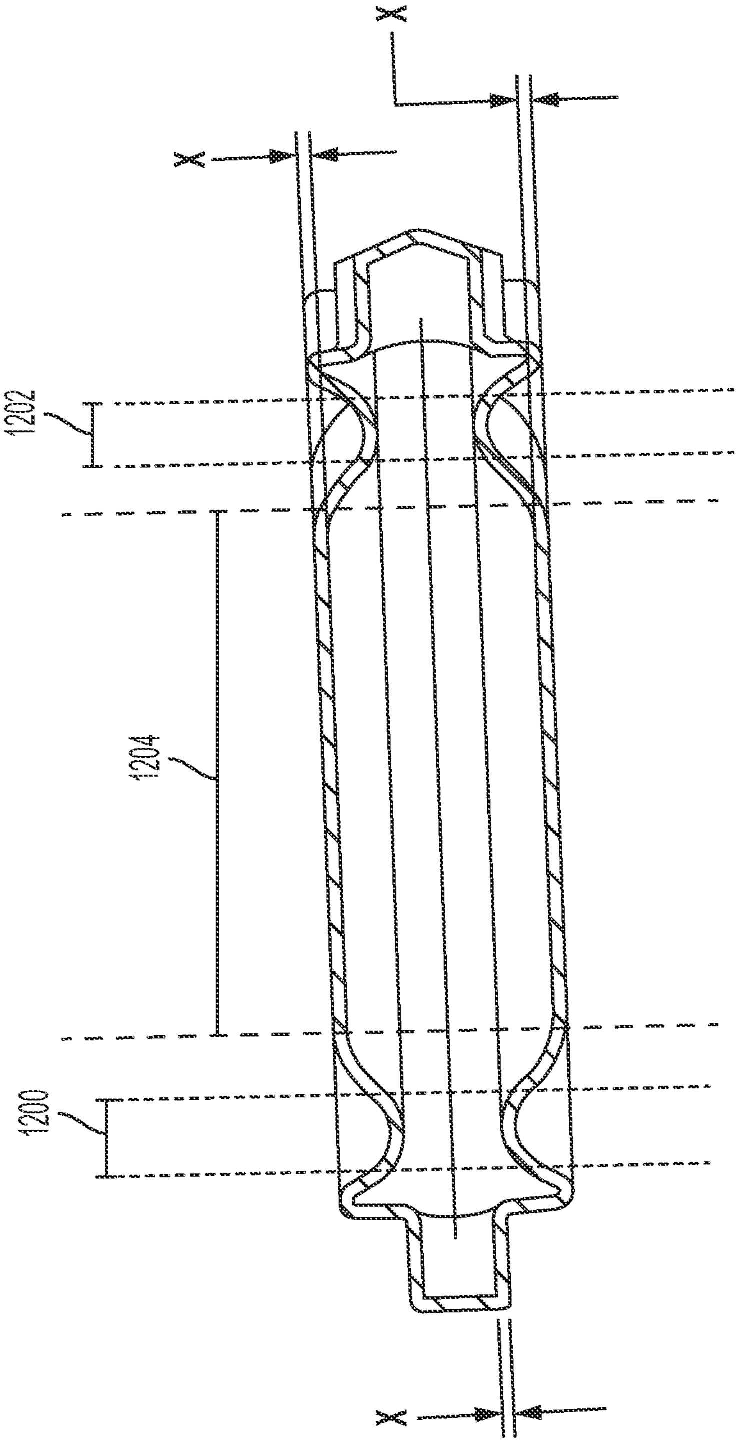

FIG. 18 is a graphical representation of the thickness of the wall of one embodiment of the blowmolded reservoir.

Like reference symbols in the various drawings indicate like elements.

DETAILED DESCRIPTION

In various embodiments, a blowmolded reservoir may be used in conjunction with an infusion device and system and methods thereof. In various embodiments, the infusion device is configured to be inserted into the subcutaneous layer of a user's skin and be fluidly connected to a fluid source. In various embodiments, the infusion device may be fluidly connected to a length of tubing and/or to an infusion pump. Infusion pumps include any infusion pump which may include, but is not limited to, the various infusion pumps and systems and methods thereof, including disposable housing assemblies, reservoirs, filling aids, charging systems, etc., shown and described in: U.S. patent application Ser. No. 13/788,260, filed Mar. 7, 2013 and entitled Infusion Pump Assembly, now U.S. Publication No. US-2014-0107579, published Apr. 17, 2014; U.S. Pat. No. 8,491,570, issued Jul. 23, 2013 and entitled Infusion Pump Assembly; U.S. Pat. No. 8,414,522, issued Apr. 9, 2013 and entitled Fluid Delivery Systems and Methods; U.S. Pat. No. 8,262,616, issued Sep. 11, 2012 and entitled Infusion Pump Assembly; and U.S. Pat. No. 7,306,578, issued Dec. 11, 2007 and entitled Loading Mechanism for Infusion Pump; all of which are hereby incorporated herein by reference in their entireties. In various embodiments, the various embodiments of the infusion devices described herein may be used alone or in conjunction with a blowmolded reservoir.

In various embodiments, a blowmolded reservoir is disclosed that includes a reservoir that is produced using a blowfill seal technique. A blowfill seal technique includes extruding molten plastic into a parasin, then, while the plastic is molten, clamping a mold onto the molten plastic and inflating the molten plastic to a shape. In some embodiments, the plastic reservoir/blowmolded reservoir may simultaneously be filled while being formed. However, in various embodiments, the blowmolded reservoir may be formed and filled at a later time, i.e., a time after formation is completed. The plastic material used may be any plastic, including, but not limited to, one or more of a rigid plastic or a collapsible plastic.

In various embodiments, the blowmolded reservoir may be configured to fit within any infusion pump, including, but not limited to, any one or more disclosed and/or described in the various references incorporated herein by reference above. In some embodiments, the blowmolded reservoir may be configured to fit within a disposable housing assembly, which, in some embodiments, may be one or more of the various embodiments shown and described in various references incorporated herein by reference above. For illustration purposes, various embodiments of the blowmolded reservoir described below are described with reference to a disposable housing assembly 100 shown in FIGS. 1A-1H and FIGS. 2A-2H. The disposable housing assembly 100 includes a hinging door 102 and in some embodiments, includes one or more of the features shown and described in one or more of the embodiments of the disposable housing assembly shown and described in any one or more of the various references incorporated herein by reference above. In various embodiments, the hinging door 102 shape may be configured to optimize the force exerted upon the blowmolded reservoir when the blowmolded reservoir is inside the disposable housing assembly 100.

Still referring to FIGS. 1A-2H, in various embodiments, a blowmolded reservoir 108 is placed inside the reservoir cavity 104 and is fluidly connected to the disposable housing assembly 100 using a connection mechanism, which may include many mechanisms including, but not limited to, one of the mechanisms shown in FIGS. 3A-3G.

Referring now also to FIGS. 3A-3G, in some embodiments, the blowmolded reservoir 108 may be fluidly connected to the disposable housing assembly 100 through a needle 106 connected to the disposable housing assembly 100 and located within the reservoir cavity 104. In practice, in some embodiments, once the blowmolded reservoir 108 is placed inside the reservoir cavity 104, the hinging door 102 may be closed upon the blowmolded reservoir and this action forces the blowmolded reservoir towards the needle 106, creating a fluid connection between the blowmolded reservoir and the disposable housing assembly 100. In some embodiments, the needle 106 may include a barb 112, which may be beneficial/desirable for many reasons, including but not limited to, locking the blowmolded reservoir 108 to the disposable housing assembly 100, which may be beneficial/desirable for many reasons, including but not limited to, when the blowmolded reservoir 108 is detached from the disposable housing assembly 100 the needle is detached with the blowmolded reservoir 108 rending the disposable housing assembly 100 non-reusable. This may be beneficial/desirable for many reasons, including, but not limited to, preventing unsafe reuse of reservoirs and/or disposable housing assemblies.

Still referring to FIGS. 3A-3G, in various embodiments, the needle 106 may include one or more seals, including, but not limited to, a rubber ridge seal 116 and/or an overmolded rubber sleeve 114 that seals radially after the needle 106 pierces the port 204 of the blowmolded reservoir. In various embodiments, the blowmolded reservoir 108 may include a gasket 110 that may be pierced by the needle 106. In various embodiments, the needle 106 may be press fit into the disposable housing assembly 100 to form a seal. In various embodiments, the portion of the disposable housing assembly 100 that includes the needle 106 may be made from any materials, including, but not limited to, rubber and/or hard plastic.

In some embodiments, the blowmolded reservoir 108 may include a septum/gasket 110. The blowmolded reservoir 108 may be fluidly connected to the disposable housing assembly 100 by way of the needle 106 piercing the gasket 110. In practice, in some embodiments, once the blowmolded reservoir 108 is placed inside the reservoir cavity 104, the hinging door 102 may be closed upon the blowmolded reservoir 108 and this action forces the blowmolded reservoir 108 towards the needle 106, and the needle 106 through the gasket 110, creating a fluid connection between the blowmolded reservoir 108 and the disposable housing assembly 100.

The embodiments shown in FIGS. 3A-3G may be used in any of the embodiments of the disposable housing assembly and/or the blowmolded reservoir.

There are various embodiments of a blowmolded reservoir disclosed and described herein. These are meant to be representative embodiments and are not intended to be limiting or limited embodiments. Referring now to FIGS. 4A-8E, various views of various embodiments of the blowmolded reservoir are shown. However, many variations of the various embodiments and variations of the blowmolded reservoir are contemplated and FIGS. 4A-8E are merely representative examples of various embodiments of the blowmolded reservoir.

Referring now also to FIGS. 4A-4I, some embodiments of the blowmolded reservoir 200 may include a domed section 202 that is formed by the mold during the blowfill process. In various embodiments, the blowmolded reservoir 200 may include a port section 204 which includes an opening and in some embodiments a septum or gasket, or in other embodiments, a needle, not shown in FIGS. 4A-4I but illustrated in FIGS. 3A-3G, that is configured to fluidly attach to the disposable housing assembly 100.

In various embodiments, the port section 204 may include legs 206, 208 that interact with cars 210, 212 (see FIG. 2I) located on the underside of hinging door 102. When the hinging door 102 is closed upon the blowmolded reservoir 200 located within the reservoir cavity 104, the cars 210, 212 on the hinging door 102 grab the legs 206, 208 on the blowmolded reservoir port 204 and pulls the blowmolded reservoir 200 towards a needle 106 located in the reservoir cavity 104. This forces the needle 106 through a septum/gasket 110 located within the port section 204.

In some embodiments the hinging door 102 and/or the disposable housing assembly 100 may include one or more catch features. In some embodiments, once the hinging door 102 is closed over the reservoir cavity 104, the hinging door 102 may be locked in position preventing the hinging door 102 from opening again. In some embodiments, the hinging door 102 is prevented from opening again by the one or more catch features. Therefore, in some embodiments, the catch features may also serve as locking features and in other embodiments, locking features may be separate from the catch features.

The action of moving the hinging door 102 from a starting, first or open position (see at least FIGS. 2I-2J) to a finishing, second or closed position (see at least FIG. 1A), in some embodiments, also acts to prime the disposable housing assembly 100 with fluid contained within the blowmolded reservoir 200.

The size and shape of the blowmolded reservoirs may vary. In some embodiments, the blowmolded reservoir 200 may include a domed section 202. The domed section may be desirable/beneficial for many reasons, including, but not limited to, allowing a larger volume blowmolded reservoir in a fixed diameter dimension. This may be desirable/beneficial for many reasons, including, but not limited to, elimination of air from the blowmolded reservoir during the priming stage.

Figure 1A:
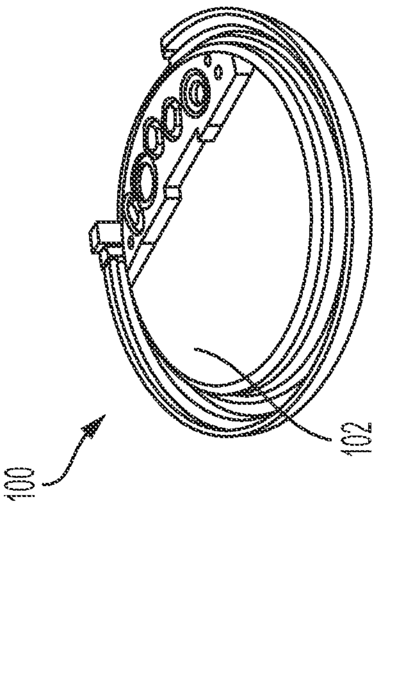
Figure 1B:
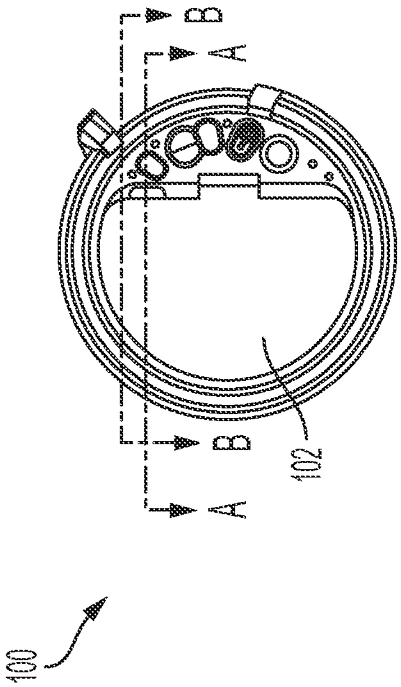
Figure 1C:
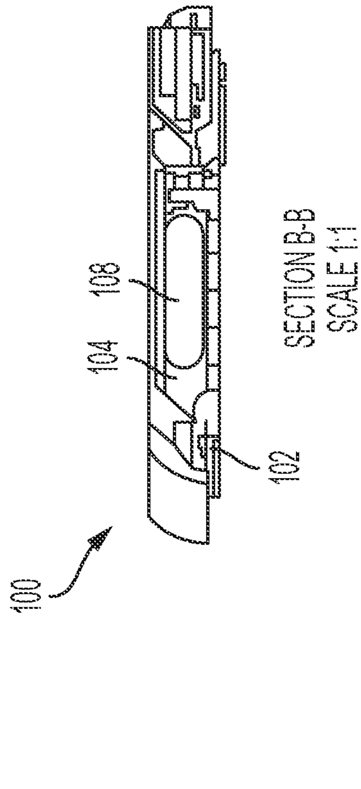
Figure 1D:
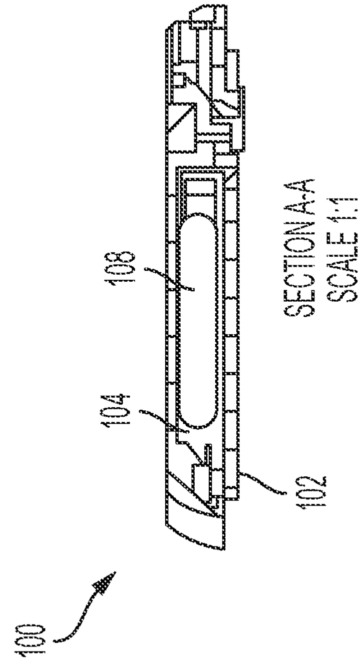
Figure 1F:
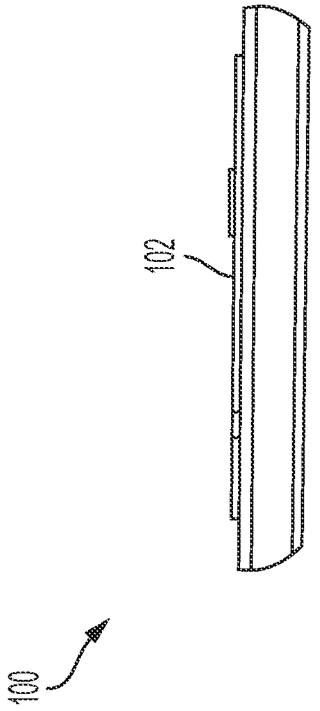
Figure 1H:
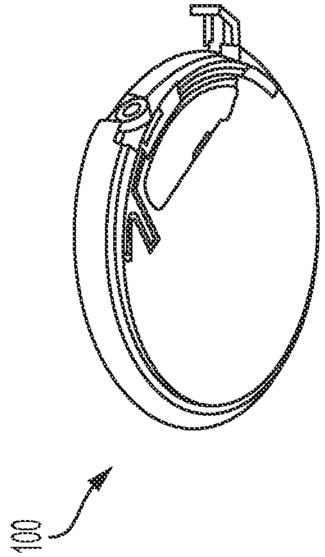
Figure 1E:
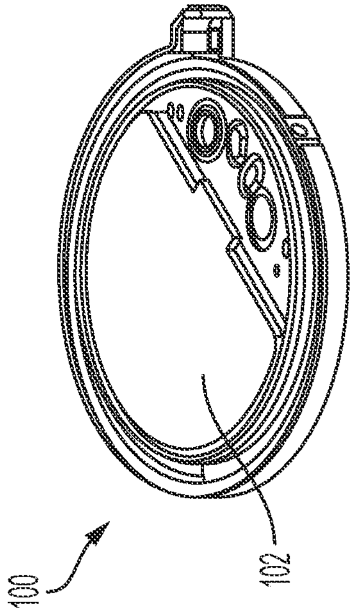
Figure 1G:
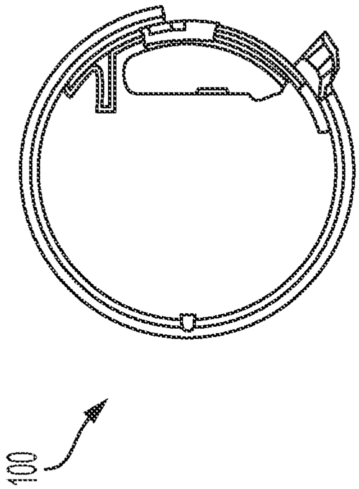
Figure 2A:
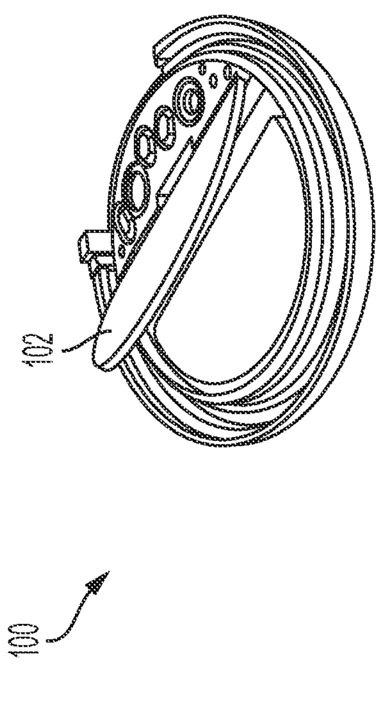
Figure 2B:
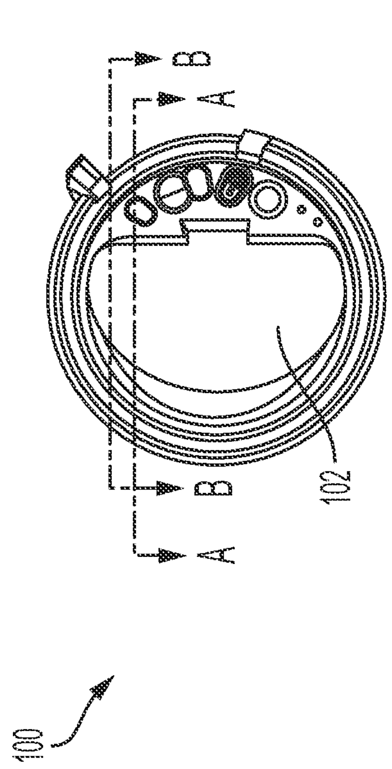
Figure 2C:
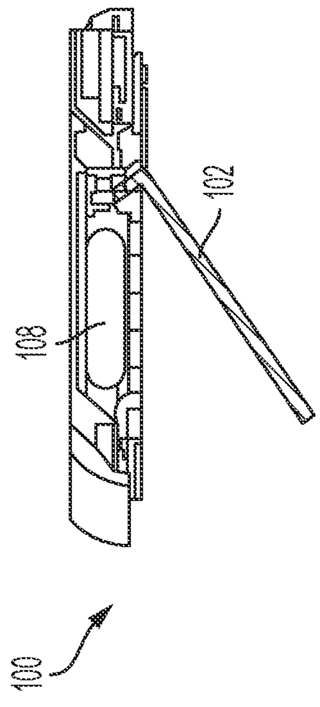
Figure 2D:
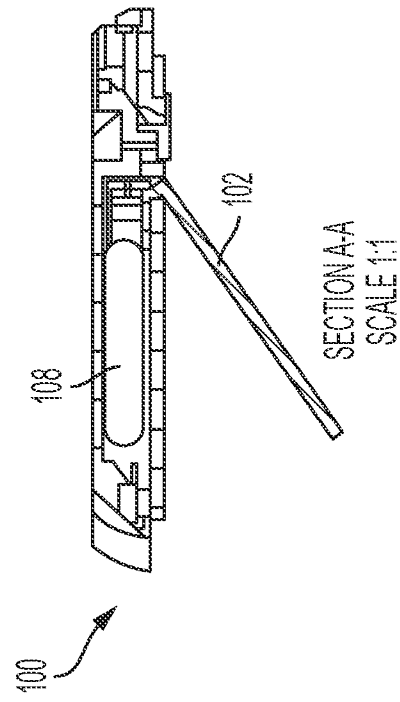
Figure 2F:
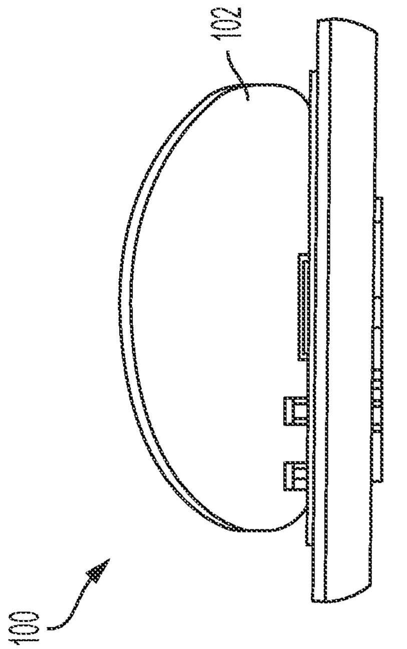
Figure 2G:
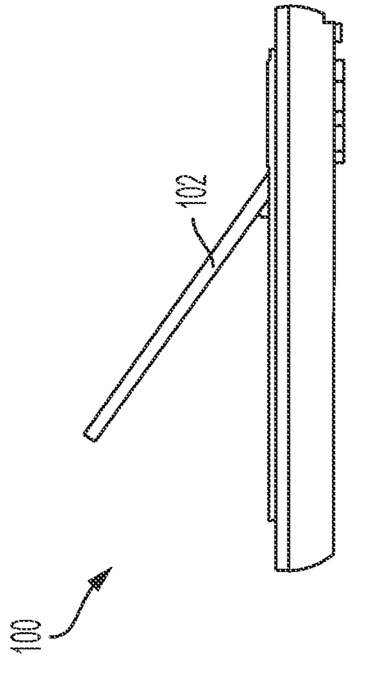
Figure 2E:
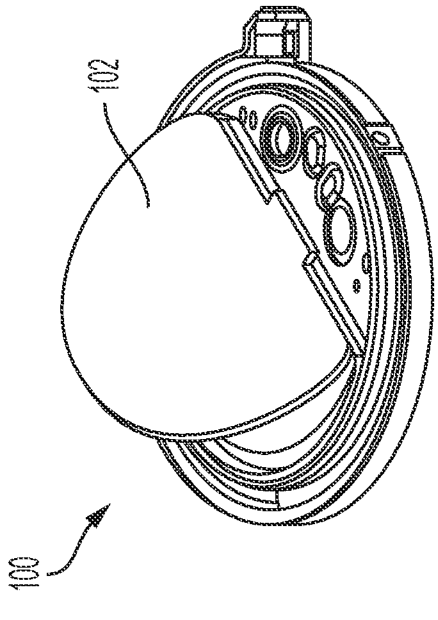
Figure 2I:
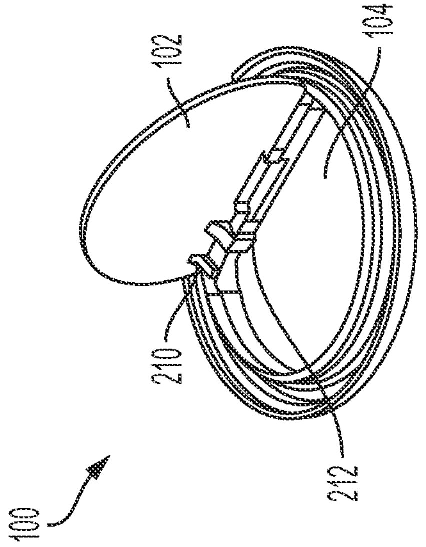
Figure 2J:
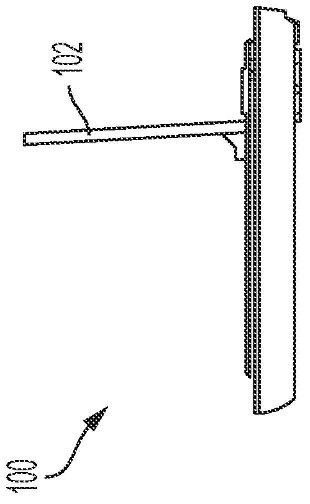
Figure 2H:
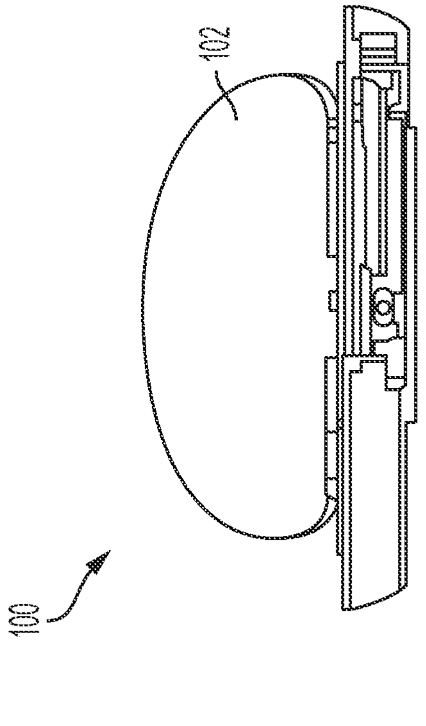
Figure 3A:
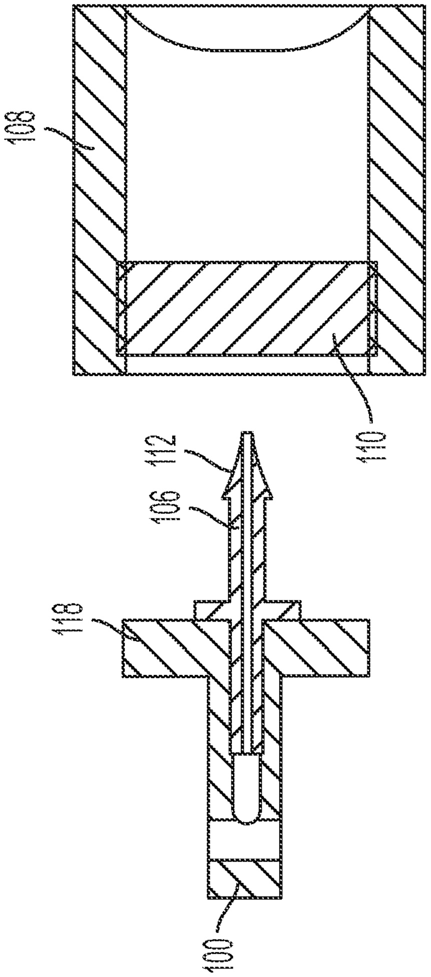
FIGS. 3A-3G are various views of one embodiment of a needle system.
Figure 3B:
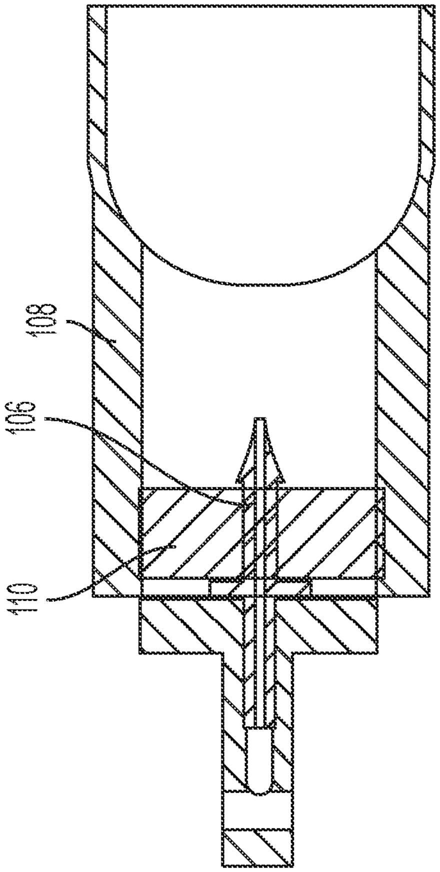
Figure 3C:
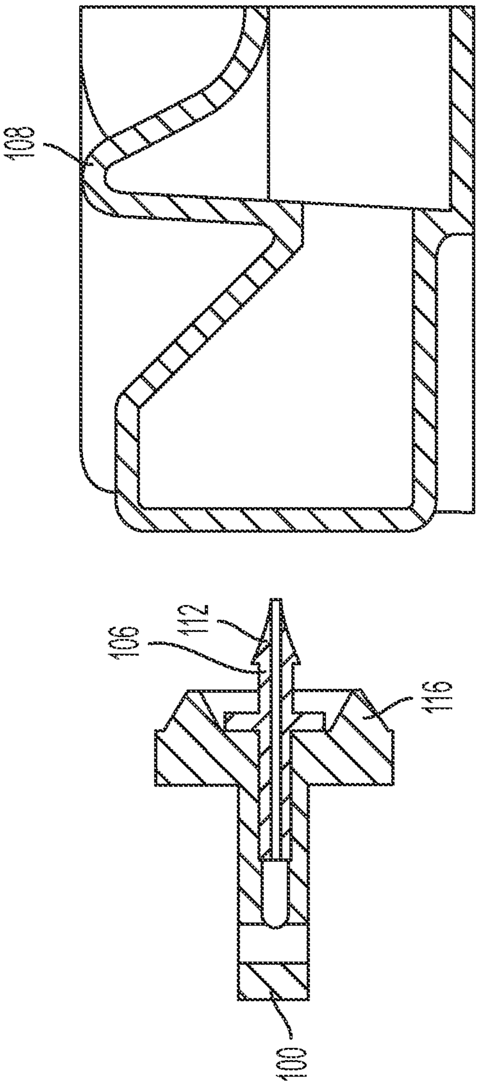
Figure 3D:
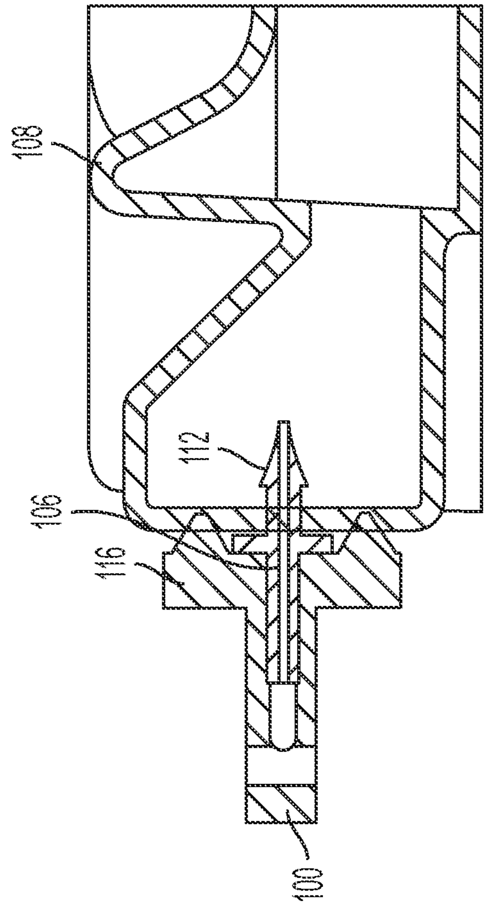
Figure 3E:
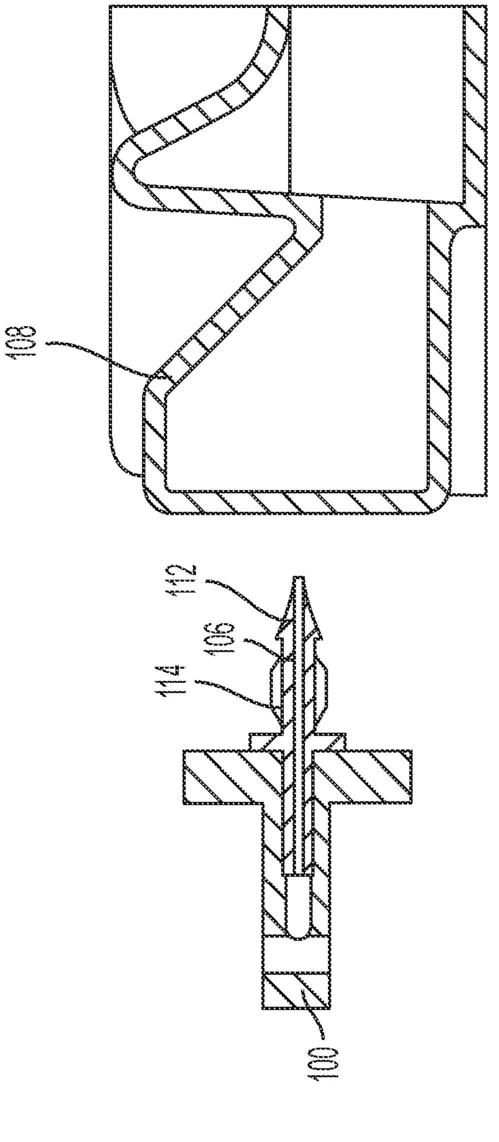
Figure 3F:
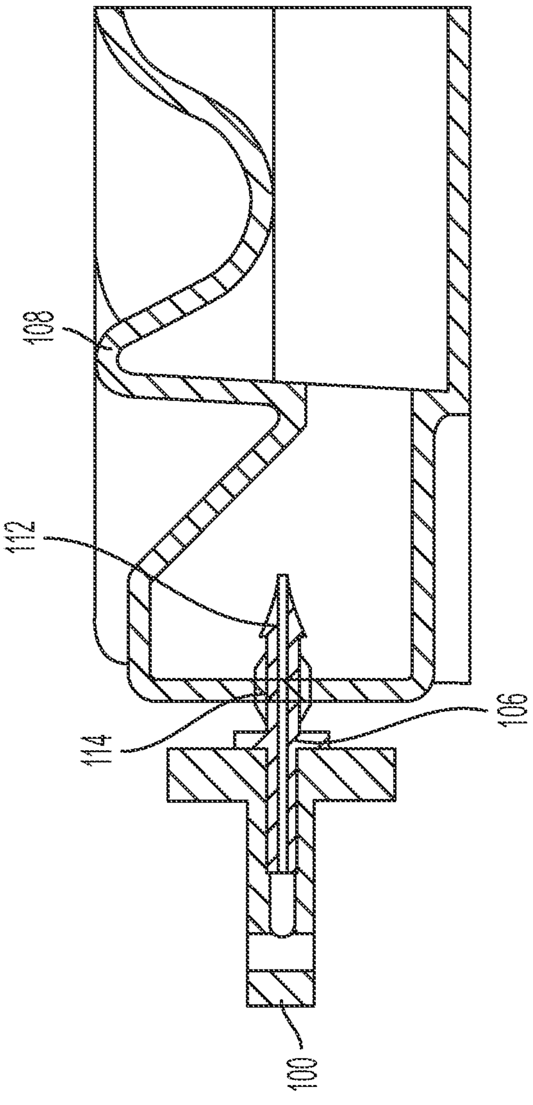
Figure 3G:
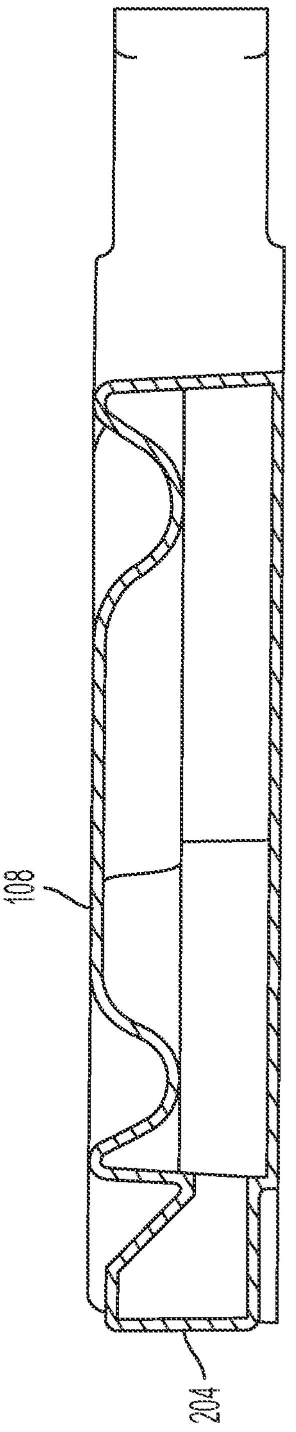
Figure 4A:
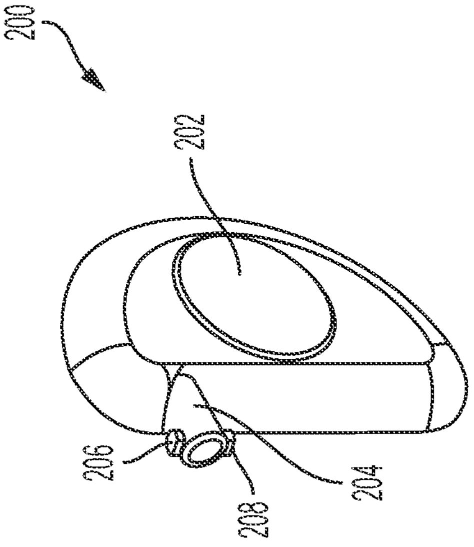
FIGS. 4A-4I are various views of one embodiment of a blowmolded reservoir.
Figure 4B:
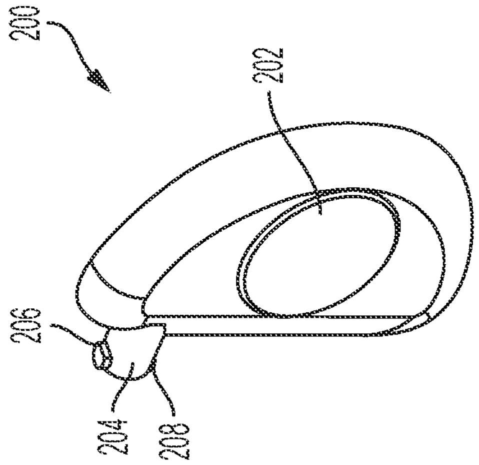
Figure 4C:
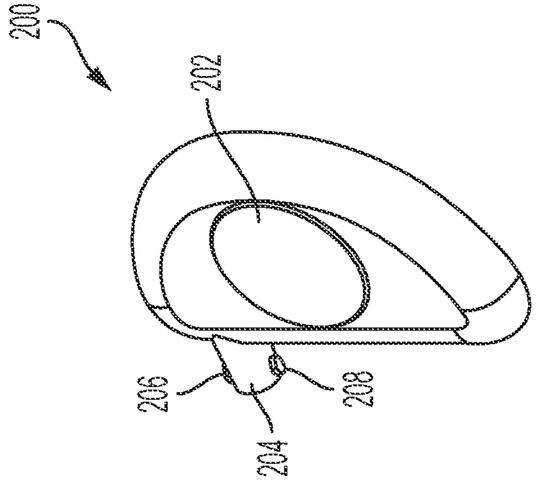
Figure 4E:
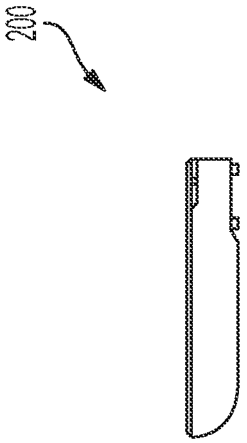
Figure 4F:
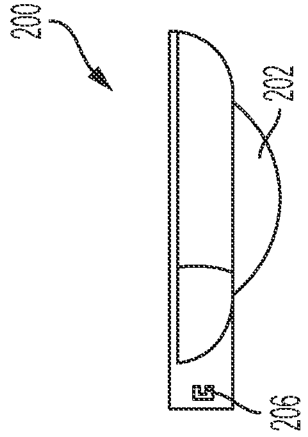
Figure 4D:
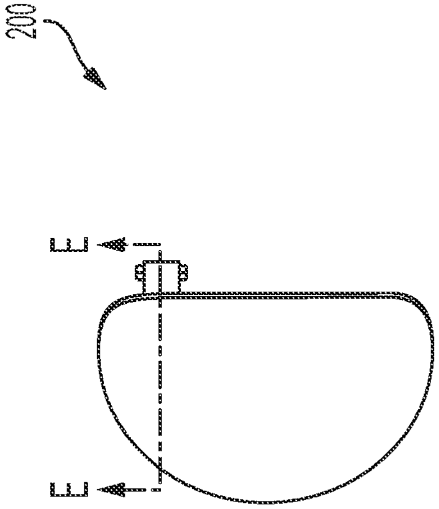
Figure 4H:
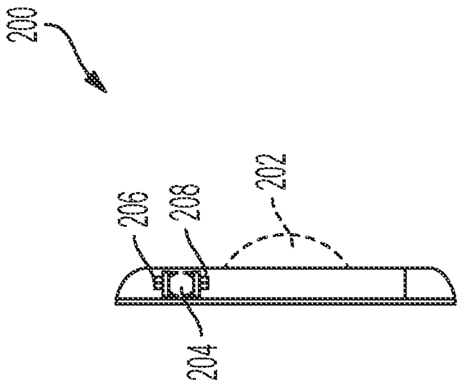
Figure 4I:
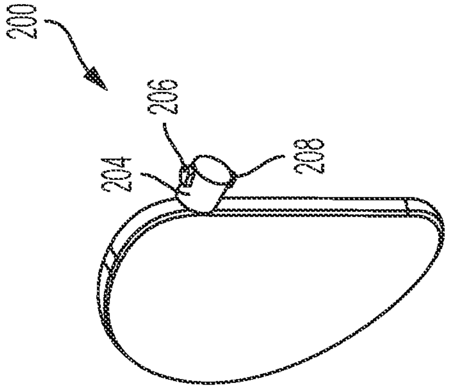
Figure 4G:
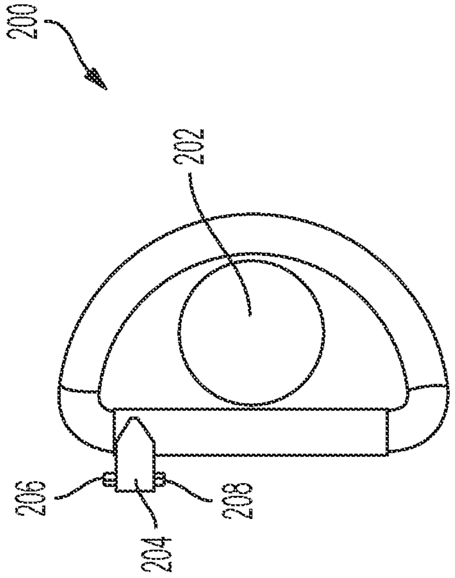
Figure 5B:
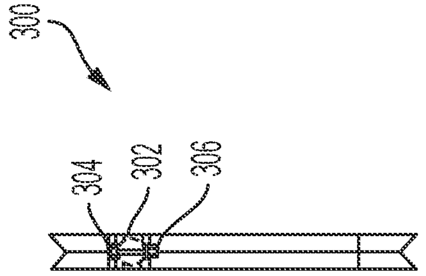
FIGS. 5A-5C are various views of one embodiment of a blowmolded reservoir.
Figure 5C:
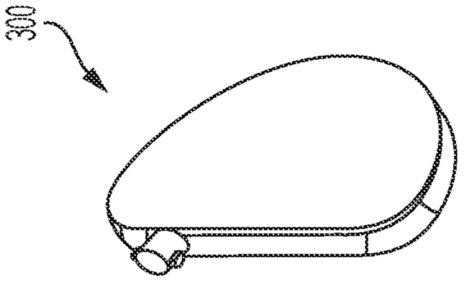
Figure 5A:
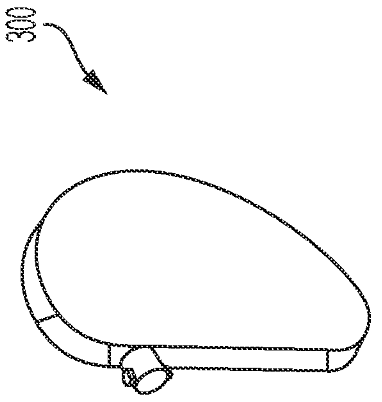
Figure 6A:
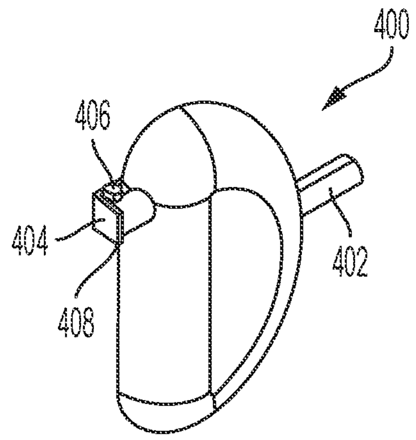
FIGS. 6A-6E are various views of one embodiment of a blowmolded reservoir.
Figure 6B:
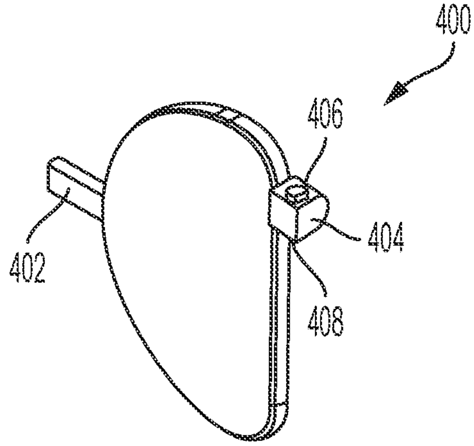
Figure 6C:
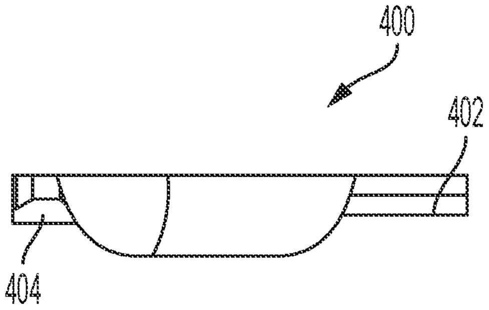
Figure 6D:
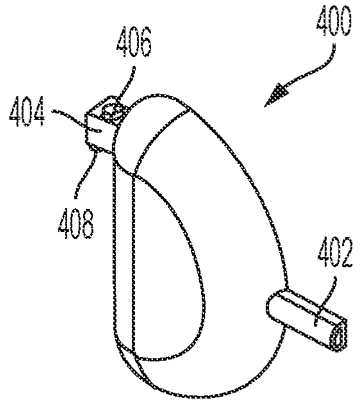
Figure 6E:
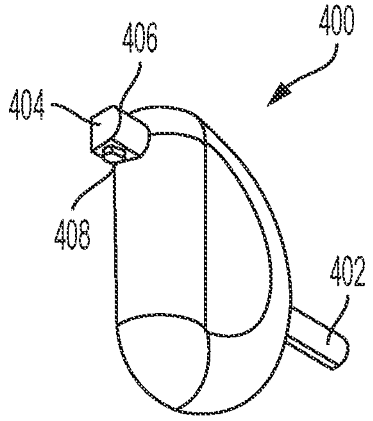

Referring now also to FIGS. 5A-5C, in some embodiments, the blowmolded reservoir 300 may include an accordion shape. This may be desirable/beneficial for many reasons, including but not limited to, the accordion shape may contribute to the blowmolded reservoir 300 collapsibility and/or configure the blowmolded reservoir 300 to collapse in a different fashion.

In various embodiments, the blowmolded reservoir 300 may include a port section 302 that includes an opening and, in some embodiments, a septum or gasket, or in other embodiments, a needle, not shown in FIGS. 5A-5C but illustrated in FIGS. 3A-3G, that is configured to fluidly attach to the disposable housing assembly 100. In various embodiments, the port section 302 may include legs 304, 306 that interact with ears 210, 212 located on the underside of hinging door 102. When the hinging door 102 is closed upon the blowmolded reservoir 300 located within the reservoir cavity 104, the ears 210, 212 on the hinging door 102 grab the legs 304, 306 on the blowmolded reservoir port 302 and pulls the blowmolded reservoir 300 towards a needle 106 located in the reservoir cavity 104. This forces the needle 106 through a septum/gasket 110 located within the port section 302.

In some embodiments the hinging door 102 and/or the disposable housing assembly 100 may include one or more catch features. In some embodiments, once the hinging door 102 is closed over the reservoir cavity 104, the hinging door 102 may be locked in position preventing the hinging door 102 from opening again.

The action of moving the hinging door 102 from a starting, first or open position (see at least FIGS. 2I-2J) to a finishing, second or closed position (see at least FIG. 1A), in some embodiments, also acts to prime the disposable housing assembly 100 with fluid contained within the blowmolded reservoir 300.

Referring now also to FIGS. 6A-6E, another embodiment of a blowmolded reservoir 400 is shown. In various embodiments it may be desirable/beneficial to include a feature that when filling the blowmolded reservoir 400 during the manufacturing process (which, in some embodiments, may be completed simultaneously with molding the blowmolded reservoir as described above, however, in other embodiments, may be completed at a later time from molding) mitigates the air that may be left in the blowmolded reservoir as a function of the manufacturing process. In some embodiments, therefore, a tail 402 may be included on the blowmolded reservoir 400. In practice, the blowmolded reservoir 400 is filled to near the top of the tail 402. The tail 402 may either be scaled or not sealed between the tail 402 and the rest of the blowmolded reservoir 400.

In various embodiments, the blowmolded reservoir 400 may include a port section 404 which includes an opening and in some embodiments a septum or gasket, or in other embodiments, a needle, not shown in FIGS. 6A-6E but illustrated in FIGS. 3A-3G, that is configured to fluidly attach to the disposable housing assembly 100. In various embodiments, the port section 404 may include legs 406, 408 that interact with cars 210, 212 located on the underside of hinging door 102. When the hinging door 102 is closed upon the blowmolded reservoir 400 located within the reservoir cavity 104, the cars 210, 212 on the hinging door 102 grab the legs 406, 408 on the blowmolded reservoir port 404 and pulls the blowmolded reservoir 400 towards a needle 106 located in the reservoir cavity 104. This forces the needle 106 through a septum/gasket 110 located within the port section 404.

In some embodiments the hinging door 102 and/or the disposable housing assembly 100 may include one or more catch features. In some embodiments, once the hinging door 102 is closed over the reservoir cavity 104, the hinging door 102 may be locked in position preventing the hinging door 102 from opening again.

The action of moving the hinging door 102 from a starting, first or open position (see at least FIGS. 2I-2J) to a finishing, second or closed position (see at least FIG. 1A), in some embodiments, also acts to prime the disposable housing assembly 100 with fluid contained within the blowmolded reservoir 400.

During the process of fluidly connecting the blowmolded reservoir 400 to the disposable housing assembly 100, in the embodiments including a tail 402, the tail 402 is pushed upwards with respect to the reservoir cavity 104 when the blowmolded reservoir 400 is initially placed within the reservoir cavity 104 and then is pushed downward when the hinging door 102 is moved to the finishing, second or closed position.

The embodiment shown in FIGS. 6A-6E include a dome-shaped blowmolded reservoir. However, various other shapes and sized may be used in conjunction with a tail embodiment.

Figure 7A:
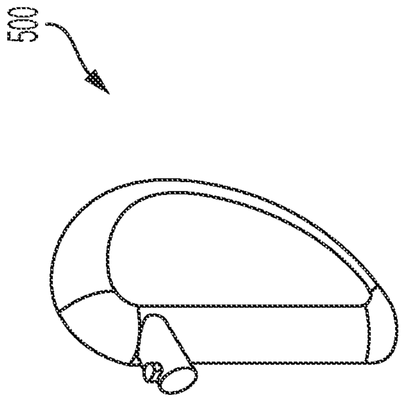
FIGS. 7A-7C are various views of one embodiment of a blowmolded reservoir.
Figure 7B:
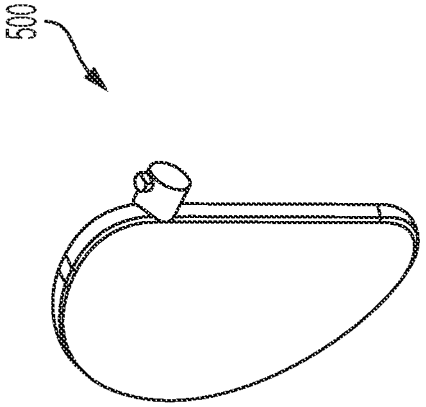
Figure 7C:
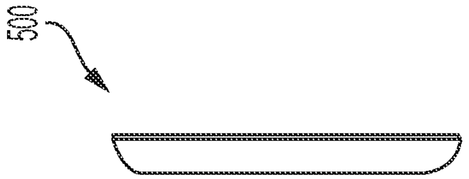

Referring now also to FIGS. 7A-7C, in some embodiments, the dome shape of the blowmolded reservoir 500, as shown, may vary. Also, in some embodiments, a dome-shaped blowmolded reservoir 500 may or may not include a tail.

Figure 8A:
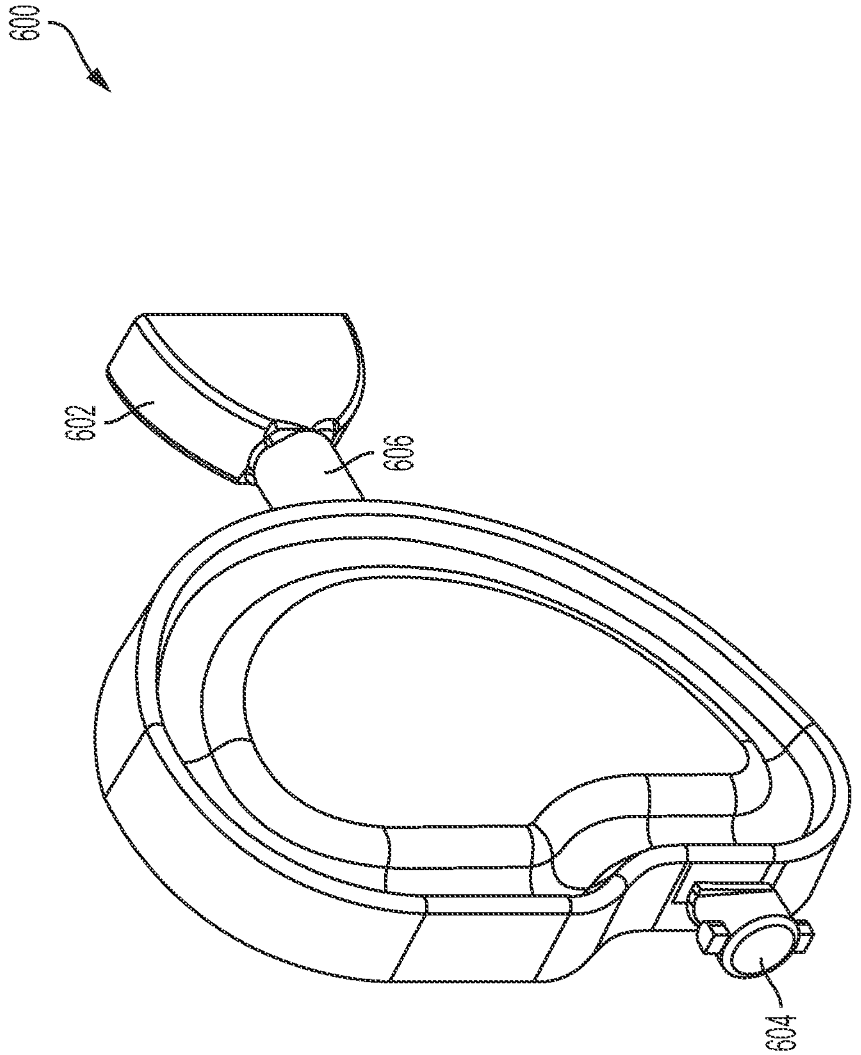
FIGS. 8A-8B are various views of one embodiment of a blowmolded reservoir.
Figure 8B:
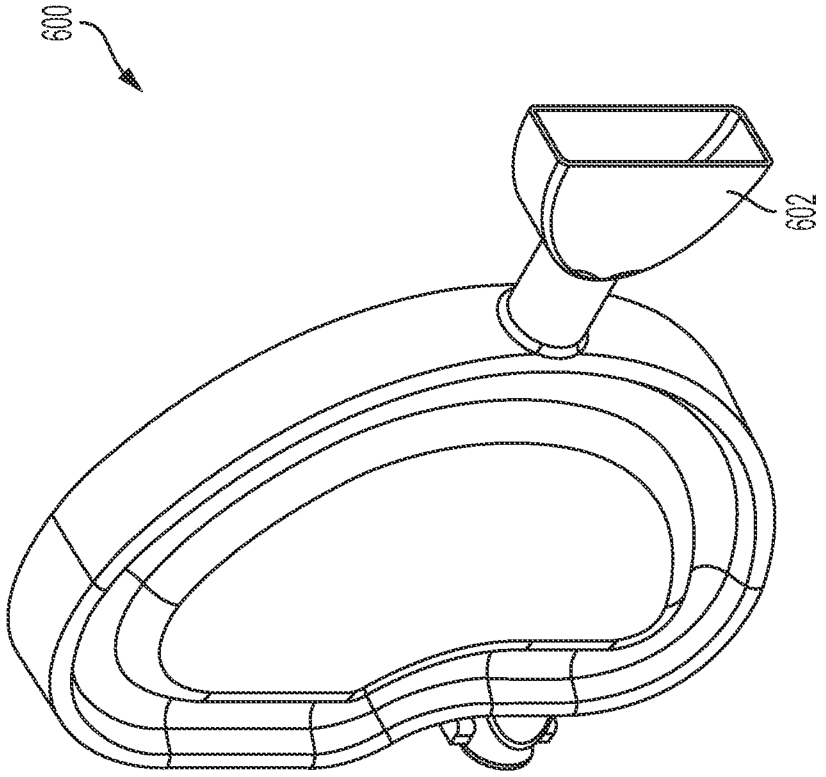

Referring now also to FIGS. 8A-8B, in some embodiments, the blowmolded reservoir 600 may include a sacrificial neck 602 that may be filled, for example, mid way or part way, and then a seal 606, or sealed area, is introduced through the fluid. In various embodiments, the seal 606 displaces the fluid. In various embodiments, a rounded-nose heat stake tool may be used to introduce the seal 606, or sealed area. In various embodiments, the heat stake tool may be made from aluminum bronze or any other material. In various embodiments, the heat stake tool may be heated to 285 degrees Fahrenheit using a heater cartridge. However, in various other embodiments, the heat stake tool may be heated to a different temperature. This embodiment may be beneficial/desirable for many reasons, including, but not limited to, the blowmolded reservoir 600 may be filled with as little air as possible. Thus, the blowmolded reservoir 600 may be filled up into the sacrificial neck 602, and then when the seal 606 is introduced, the air may be trapped in the sacrificial neck 602 and not within the blowmolded reservoir 600. Thus, in practice, when the blowmolded reservoir 600 is inserted into the disposable housing assembly 100, the sacrificial neck 602 may be removed from the remainder of the blowmolded reservoir 600, and there will not be air inside the blowmolded reservoir 600. In various embodiments, a needle 106 in the disposable housing assembly 100 will connect the blowmolded reservoir 600 to the disposable housing assembly 100 through the port 604.

Referring now also to FIGS. 15A-17G in some embodiments, the blowmolded reservoir 1020 includes a reservoir section 1028 and may include a sacrificial neck 1022, seal or sealed area, that may be filled, for example, mid way or part way, and then a seal 1026 is introduced through the fluid. In various embodiments, the seal 1026 displaces the fluid. In various embodiments, a rounded-nose heat stake tool may be used to introduce the seal 1026. In various embodiments, the heat stake tool may be made from aluminum bronze or any other material. In various embodiments, the heat stake tool may be heated to 285 degrees Fahrenheit using a heater cartridge. However, in various other embodiments, the heat stake tool may be heated to a different temperature. This embodiment may be beneficial/desirable for many reasons, including, but not limited to, the blowmolded reservoir section 1028 may be filled with as little air as possible. Thus, the blowmolded reservoir 1020 may be filled up into the sacrificial neck 1022, and then when the seal 1026 is introduced, the air may be trapped in the sacrificial neck 1022 and not within the reservoir section 1028. Thus, in practice, when the blowmolded reservoir 1020 is inserted into the disposable housing assembly 100, the sacrificial neck 1022 may be removed from the reservoir section 1028, and there will not be air inside the reservoir section 1028. In various embodiments, a needle 106 in the disposable housing assembly 100 will connect the blowmolded reservoir section 1028 to the disposable housing assembly 100 through the port 1024.

Referring now also to FIGS. 15D-17G, the reservoir section 1028 is shown. The reservoir section 1028 includes a port 1024. The sacrificial neck 1022 is shown in FIGS. 15A, 15B and 15D-15G.

In various embodiments, the blowmolded reservoir may be made from any plastic material including but not limited to polyethylene and polypropylene. In some embodiments, following manufacture and filling of the blowmolded reservoir, a cap or other cover may be connected and/or attached to the port section. In some embodiments where a septum/gasket is inside the port section, the septum/gasket may be added as part of the blowmolded seal process or added after the process is completed. In some embodiments, the blowmolded reservoir may include a bottom section and a top section. In various embodiments, the bottom section of the various embodiments of the blowmolded reservoir may be hard and the top section may be flexible and/or collapsible. In some embodiments, one side of the blowmolded reservoir may be thicker than the other. In some embodiments, the top and bottom of the blowmolded reservoir may be thicker than the side walls. This may be desirable/beneficial for many reasons, including but not limited to, increasing the collapsibility of the blowmolded reservoir.

In various embodiments, the blowmolded reservoir may be filled by connecting the blowmolded reservoir to a blister pack containing a fluid and squeezing the fluid into the blowmolded reservoir. In some embodiments, the blister pack may include a needle that pierces a septum/gasket located in the blowmolded reservoir.

In some embodiments, a barrier layer may be added to the reservoir cavity and a fluid and/or therapeutic fluid may be added to the reservoir cavity such that the fluid is maintained between the reservoir cavity and the barrier layer.

Fluidly Connecting Blowmolded Reservoir to Disposable

In various embodiments, the blowmolded reservoir may be fluidly connected to a disposable housing assembly, which may include any disposable housing assembly described herein and/or any disposable housing assembly described and/or shown in any one or more of various references incorporated herein by reference above. Various embodiments for fluidly connecting the blowmolded reservoir to the disposable housing assembly are described below and with reference to FIGS. 9A-12D.

Referring now also to FIGS. 9A-9G, a disposable housing assembly 700 is shown with a blowmolded reservoir 702 and a cover 704. In various embodiments, the blowmolded reservoir 702 is made from low density polyethylene (LDPE). A luer 706, which can attach to any infusion set known in the art, wherein infusion sets include at least a cannula, which may be fluidly connected to tubing 708, is fluidly connected to the blowmolded reservoir 702. The luer 706 may be connected to an infusion set (not shown) which is inserted into a user for delivery of fluid from the blowmolded reservoir 702 into the user. In some embodiments, only the tubing 708 is attached to the disposable housing assembly 700. In some embodiments, the tubing 708 is not attached to the disposable housing assembly 700 but may be attached at a later time, e.g., after the infusion set is inserted into the user.

Figure 9A:
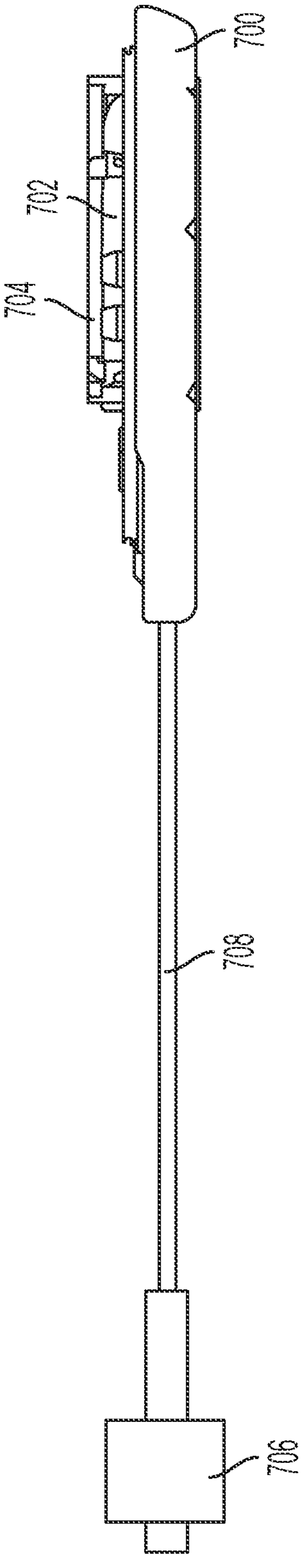
FIGS. 9A-9G are various views of one embodiment of a disposable housing assembly.
Figure 9B:
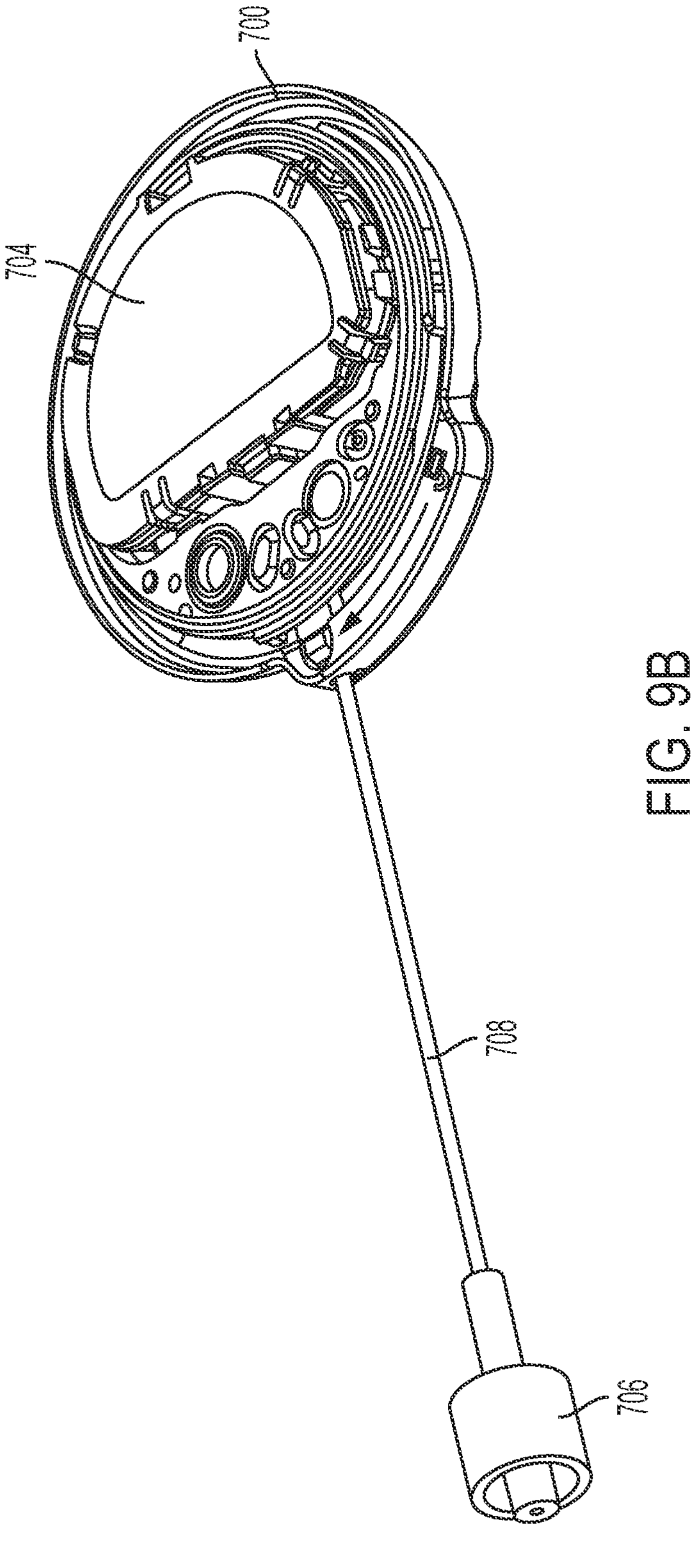
Figure 9C:
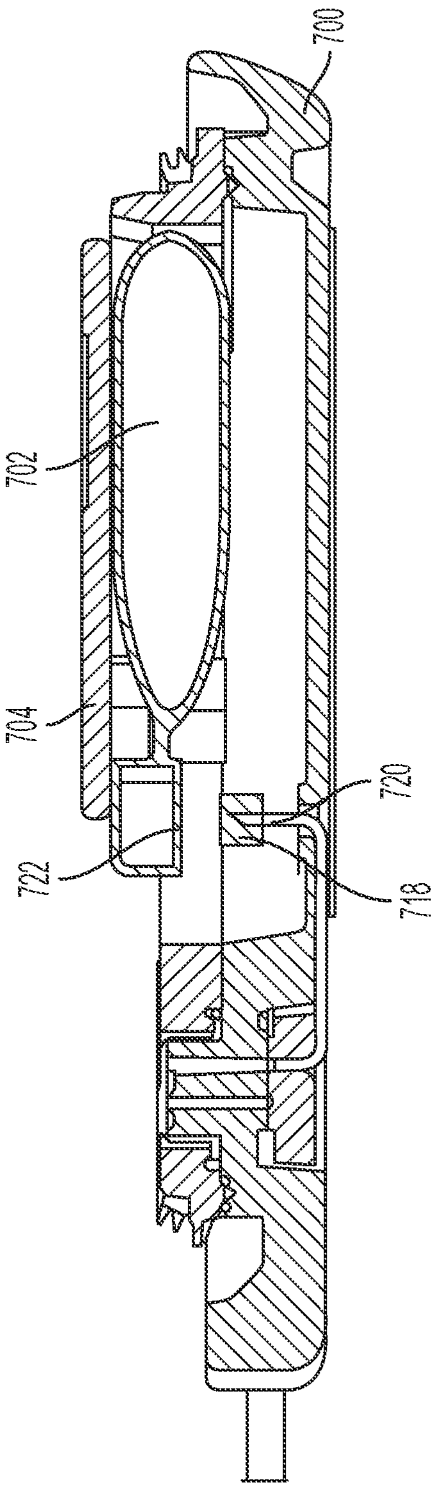
Figure 9D:
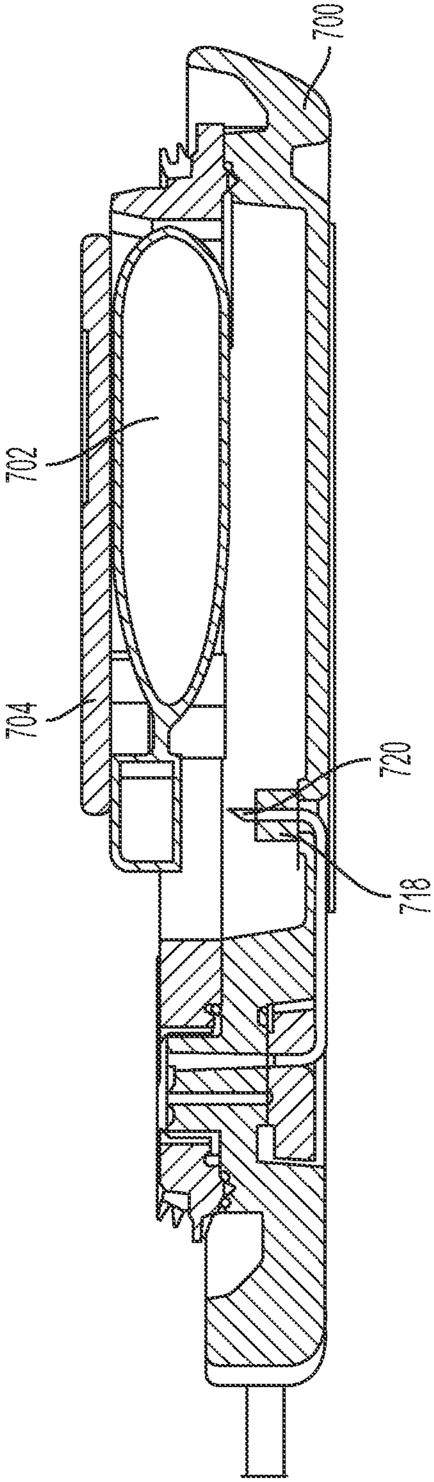
Figure 9E:
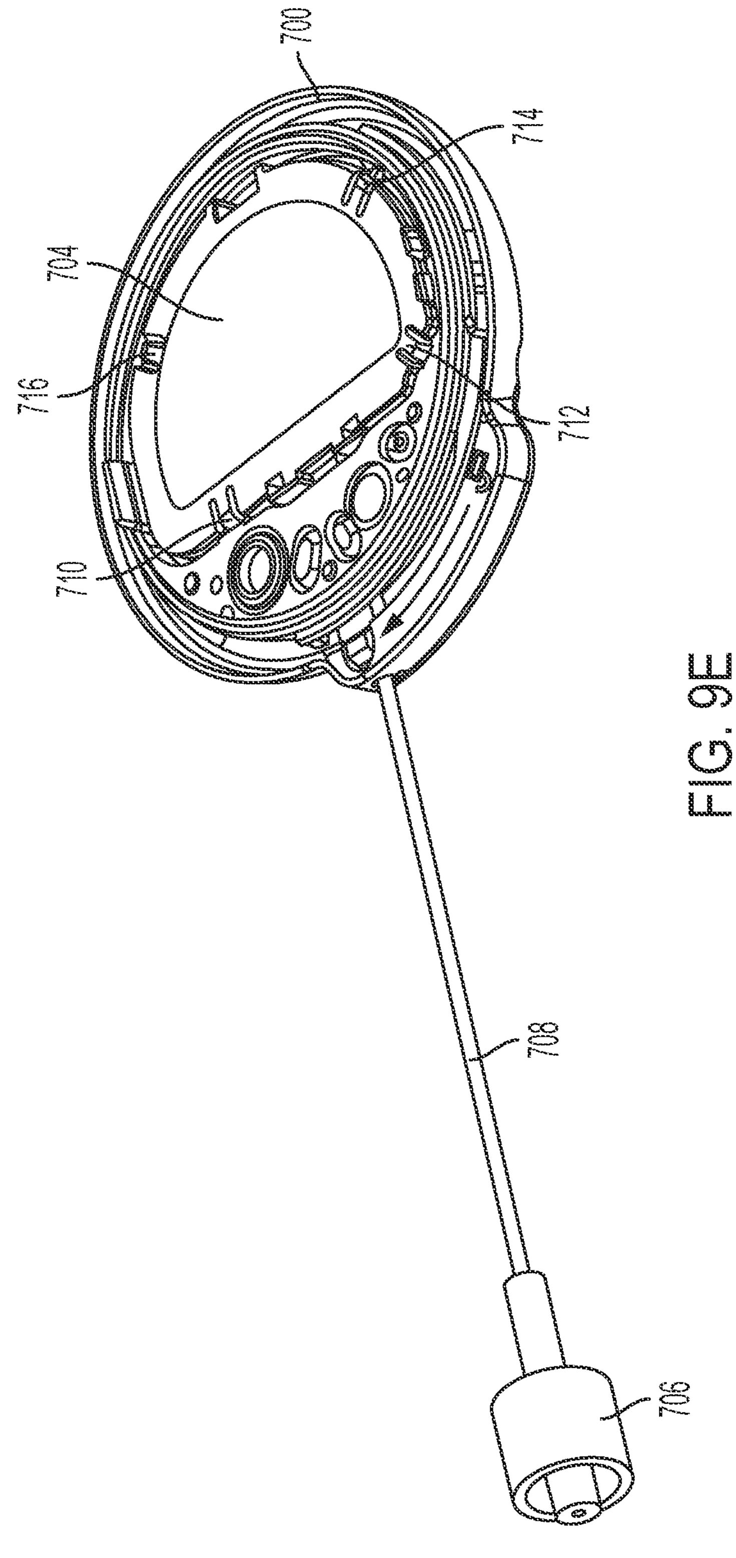
Figure 9F:
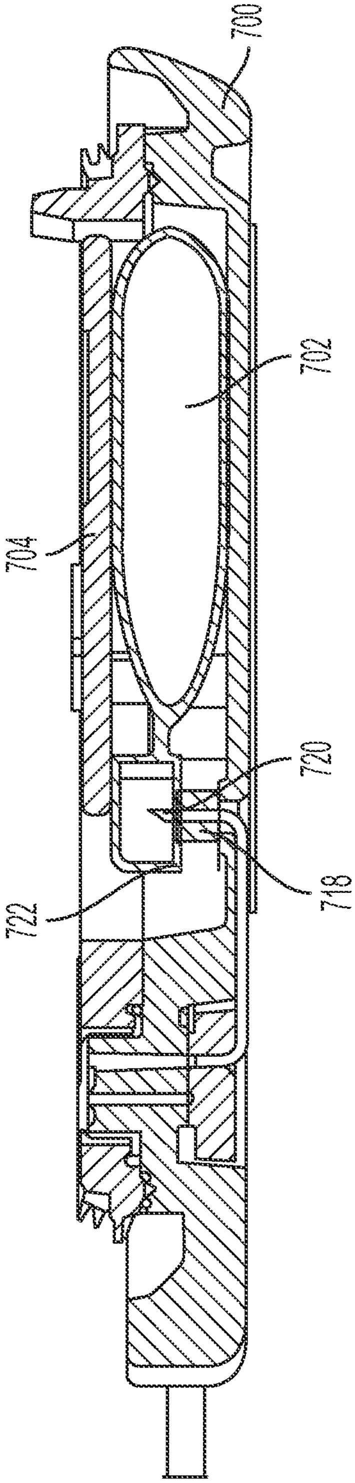
Figure 9G:
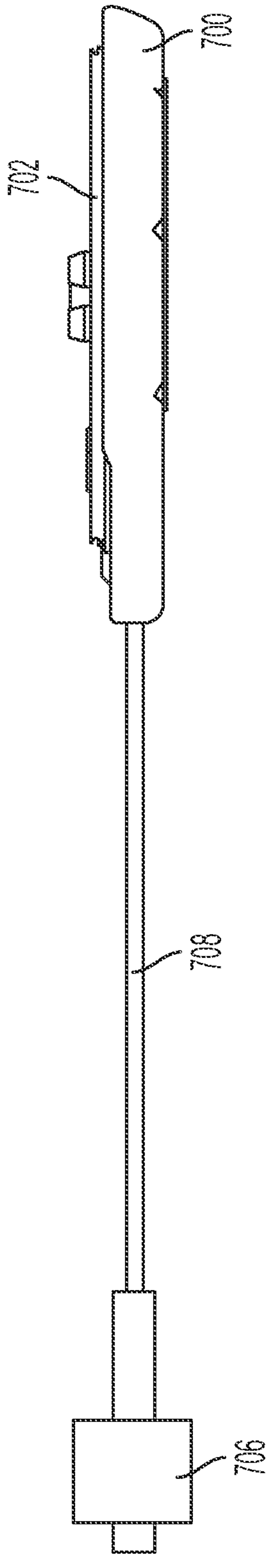

Referring to FIGS. 9A-9D, the disposable housing assembly includes a cover 704, shown in its first and unactuated position, which maintains the position of the blowmolded reservoir 702. The disposable housing assembly 700 includes a needle 720 and a gasket 718. In some embodiments, one end of the needle 720 may be located inside the gasket 718, as shown in FIG. 9C. However, in other embodiments, one end of the needle 720 may be located outside of, but in communicative relation to, the gasket 718. Regardless, in operation, when force is applied to the cover 704, the cover 704 moves from a first and unactuated position, as shown in FIGS. 9A-9D, to a second or actuated position as the cover 704 presses downward on the blowmolded reservoir 702 and this force pushes the end of the needle 720 through a point in the blowmolded reservoir 702, which may include point 722. The force exerted on the blowmolded reservoir 702 is also translated to the gasket 718 which is crushed between the disposable housing assembly 700 and the blowmolded reservoir 702. The force moves the cover 704 from the first and unactuated position to the second and actuated position, as shown in FIGS. 9E-9G. The force also moves the blowmolded reservoir 702 from an unactuated position to an actuated position.

In various embodiments, the blowmolded reservoir 702 connection to the needle 720 is sealed primarily by piercing the blowmolded reservoir 702. However, the gasket 718 acts as a secondary seal. This is beneficial/desirable for many reasons, including but not limited to, if the needle 720 and blowmolded reservoir 702 do not form a perfect seal, the gasket 718 provides an additional and/or secondary seal.

Various embodiments include a needle 720 which includes a sharp end, as shown in FIGS. 9A-9E, and a second end which may be sharp or blunt. The second end connects the needle 720 to a fluid path in the disposable housing assembly 700. The fluid path connects the contents of the blowmolded reservoir 702 to a luer 706, which, in various embodiments, may be attached to any infusion set and in some embodiments, an infusion set may include any entry into a user for delivery of fluid contained within a blowmolded reservoir 702.

Referring now also to FIGS. 9B and 9E, in various embodiments, the cover 704 may include catch features 710, 712, 714, 716 which, once the cover 704 is moved to the second or actuated positions, maintains the cover 704 in the second or actuated position. In various embodiments, the cover 704 includes four catch features 710, 712, 714, 716, however, in various other embodiments, the cover 704 may include more than four or less than four catch features. In some embodiments, the catch features 710, 712, 714, 716 may be designed as shown, however, in various embodiments, the catch features may be any type of catch, latch and/or snap, and/or any feature that maintains the cover 704 in the second or actuated position. In various embodiments, the cover 704 may be captured in any one or more various ways. Thus, any one or more feature that locks/maintains the cover 704 in the second or actuated position may be used.

The catch features 710, 712, 714, 716 may be beneficial/desirable for many reasons, including, but not limited to, the catch features 710, 712, 714, 716 maintain the cover 704 in the second or actuated position, and this prevents reuse of the disposable housing assembly 700 and/or blowmolded reservoir 702. The catch features 710, 712, 714, 716 also hold the blowmolded reservoir 702 in the unactuated position.

Referring now also to FIGS. 10A-10M, another embodiment for fluidly connecting a blowmolded reservoir 802 to a disposable housing assembly 800 is shown. In this embodiment, which also includes a cover 804, the cover 804 moves horizontally, or slides, to fluidly connect a blowmolded reservoir 802 to a disposable housing assembly 800. In various embodiments, the blowmolded reservoir 802 is made from low density polyethylene (LDPE). Also, although not shown, in various embodiments, the disposable housing assembly 800 may be attached to a tubing and the tubing attached to a luer, and the luer attached to an infusion set. In various embodiments, the system may or may not include tubing.

Referring to FIGS. 10A-10G, to the extent the cover 804 is depicted, the cover 804 is in the first or unactuated position. The cover 804 includes a needle holder feature 815, a support feature 806 and a catch feature 808. The disposable housing assembly 800 includes a mating catch feature 816, a mating support feature 818, and a support block 820 in the reservoir cavity for the blowmolded reservoir 802.

Figure 10A:
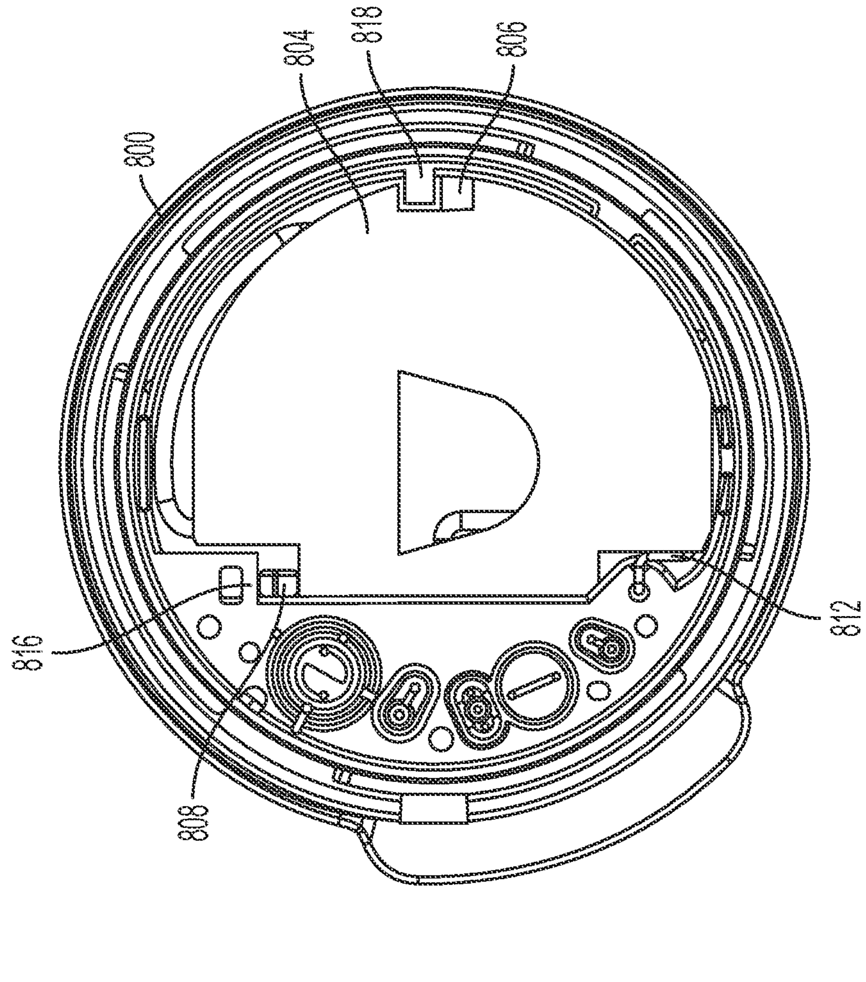
FIGS. 10A-10M are various views of one embodiment of a disposable housing assembly.
Figure 10B:
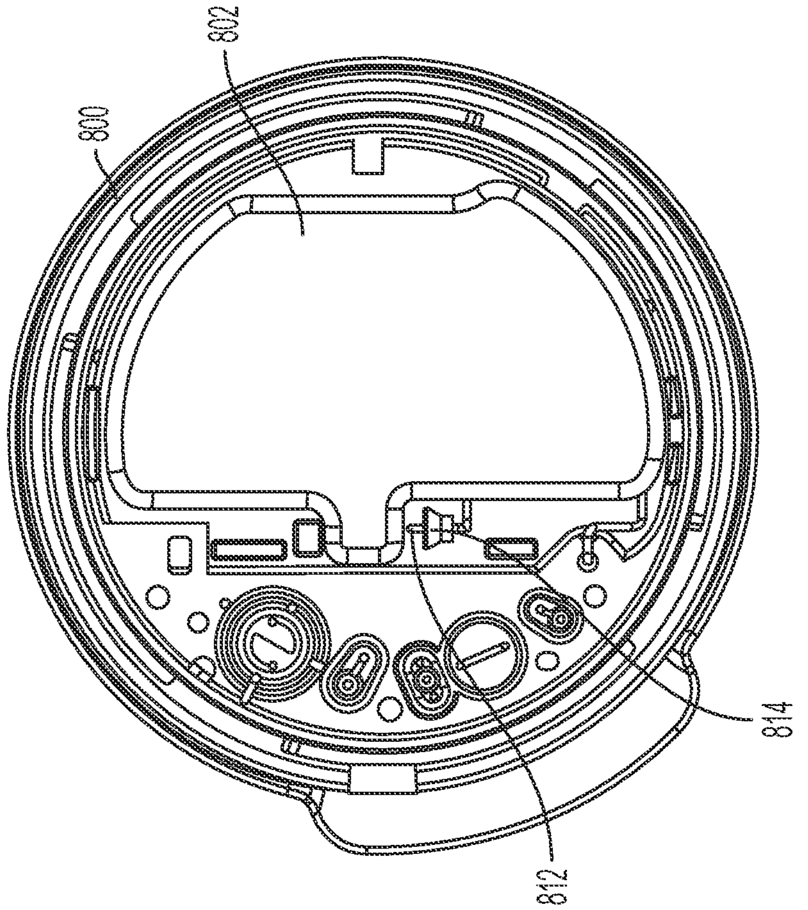
Figure 10C:
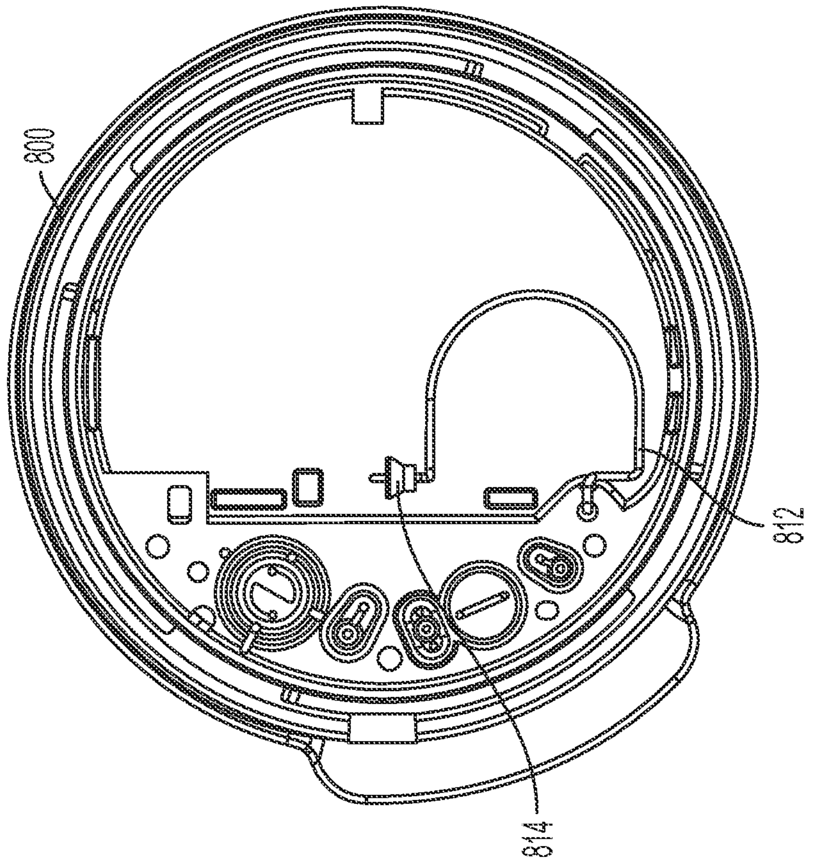
Figure 10D:
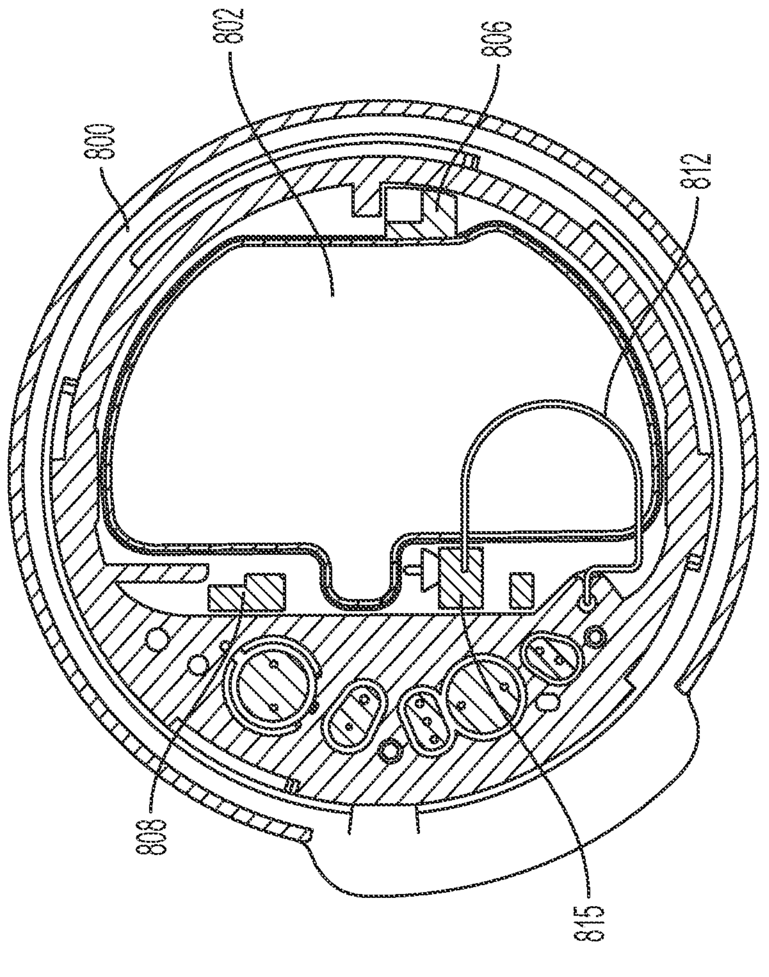
Figure 10E:
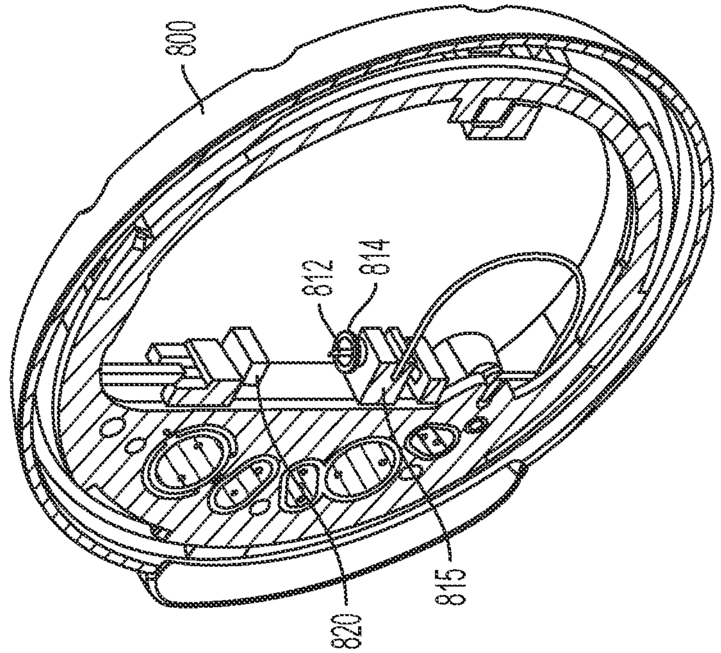
Figure 10F:
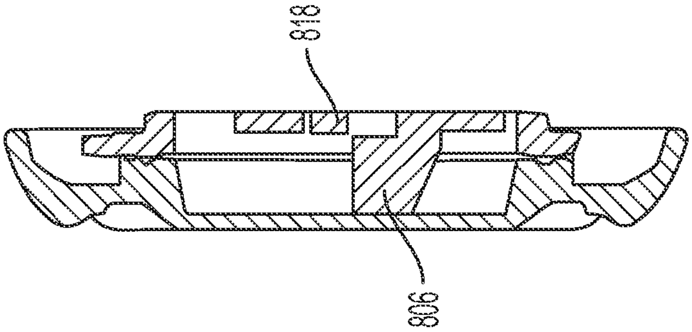
Figure 10G:
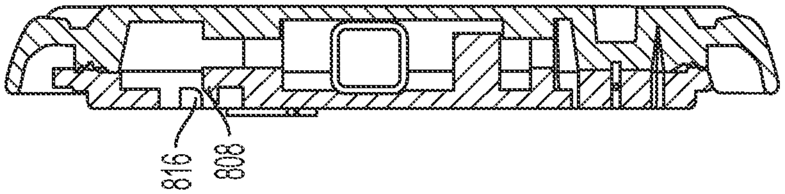
Figure 10H:
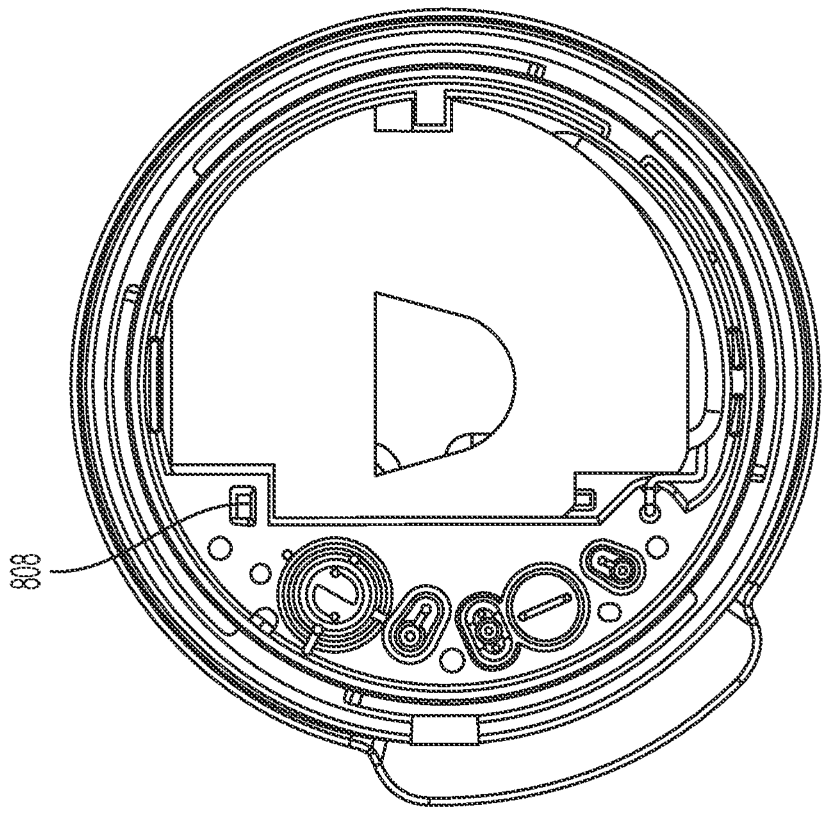

In various embodiments, the shape of the needle 812 may be as shown in FIGS. 10A-10M, or may be various other shapes and sizes. In the embodiments shown in FIGS. 10A-10G, the needle 812 includes an end that is attached to a gasket 814. In some embodiments, the gasket 814 and needle 812 may be as shown in FIGS. 10A-10G, however, in other embodiments, the tip of the needle 812 may be inside the gasket 814 in the first or unactuated position. The remaining body of the needle 812 rests on top of the reservoir 802, as shown in FIG. 10D.

Figure 10I:
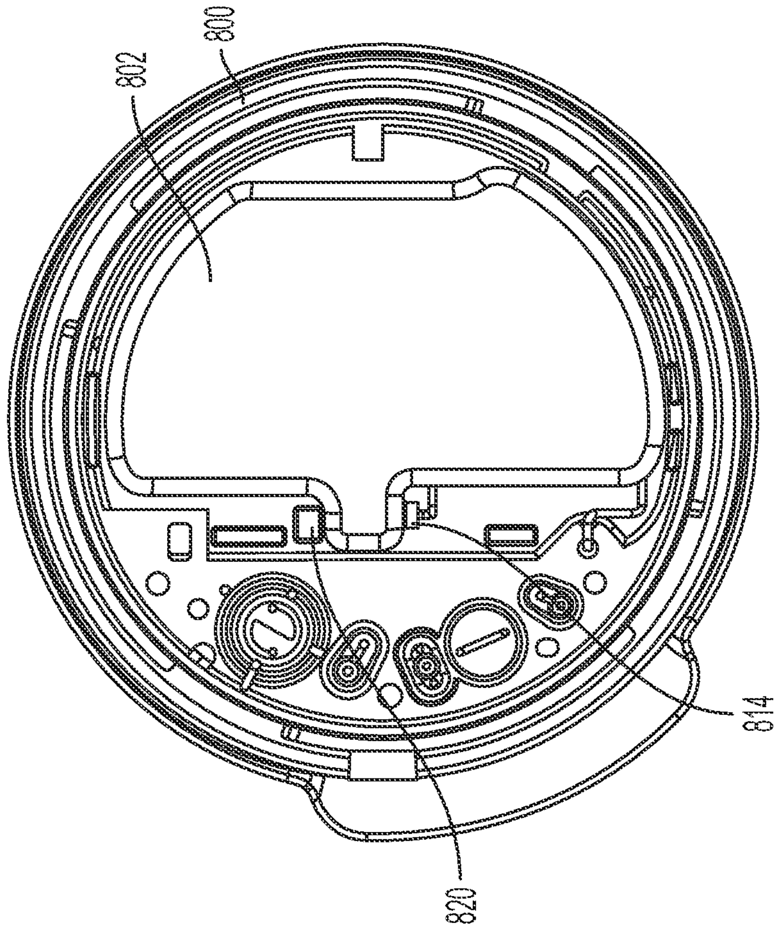
Figure 10J:
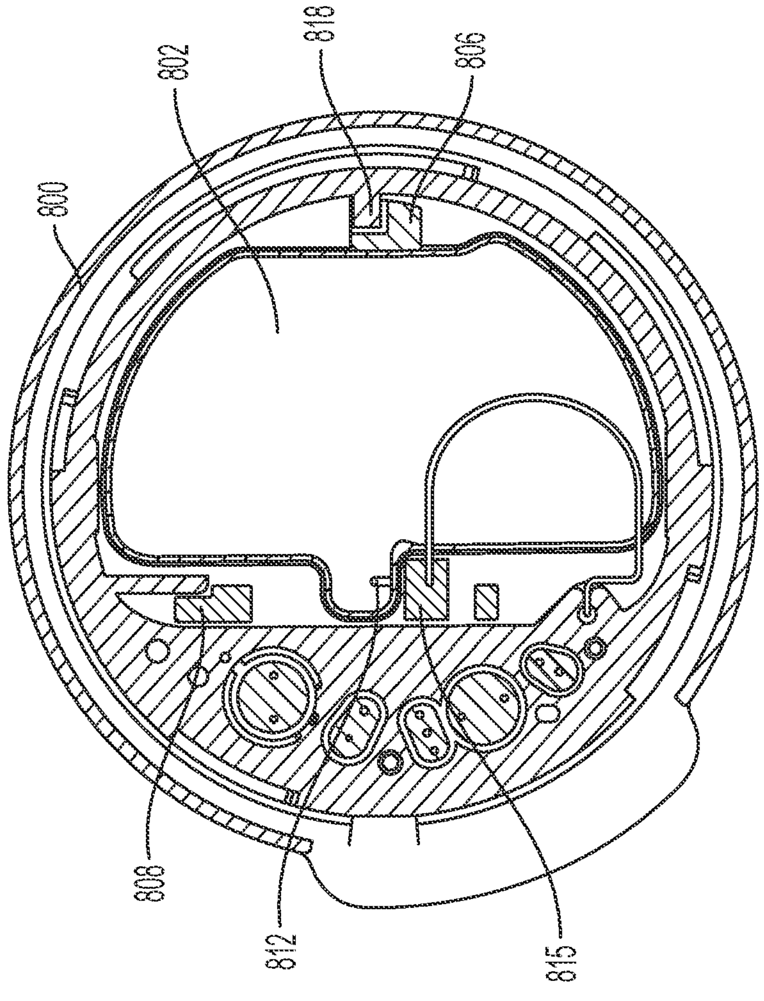
Figure 10K:
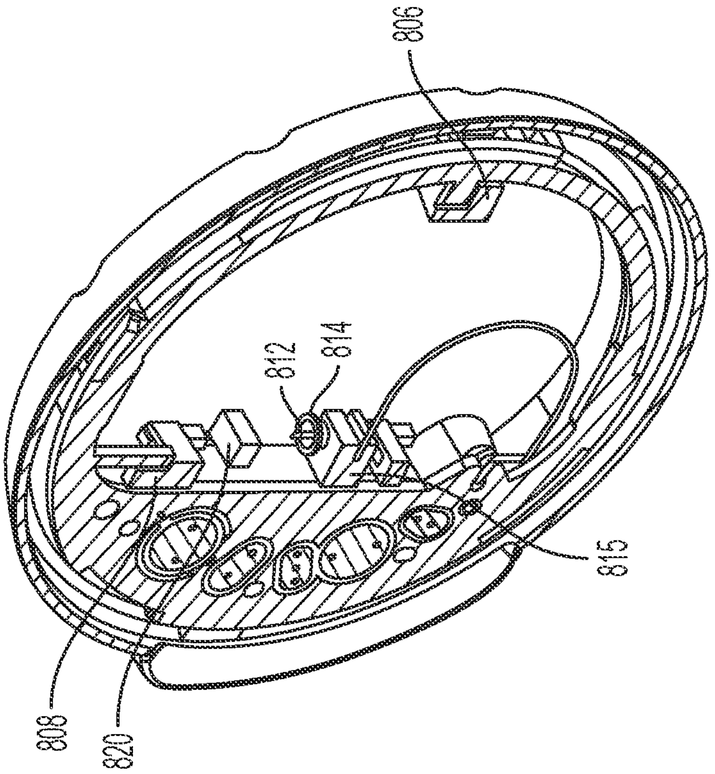
Figure 10L:
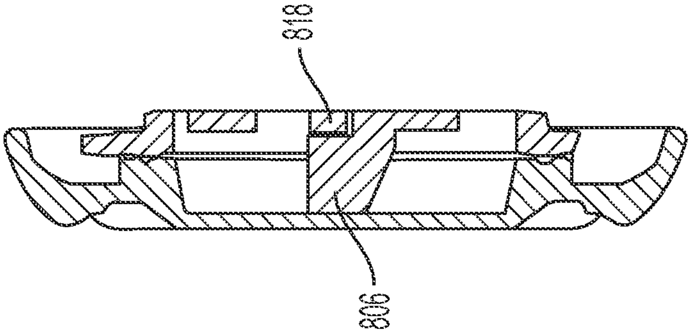
Figure 10M:
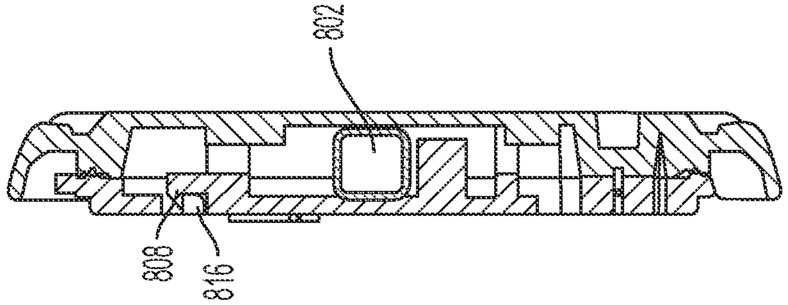

Referring now also to FIGS. 10H-10M, the cover 804 has moved to the second or actuated position. In FIGS. 10I and 10J, the cover 804 is not shown, however, the other parts of the device are shown in the actuated position. In FIG. 10K, the reservoir 802 is not shown and some features of the cover are shown, however, the entire cover is not shown. However, the other parts of the device are shown in the actuated position.

The cover 804 moves from the first or unactuated position to the second or actuated position with the application of force on the cover 804. In the second or actuated position, the cover 804 has moved in the horizontal direction, and the force of the cover 804 pushes the needle 812 such that it pierces through the reservoir 802. The force exerted on the cover 804 is also translated to the gasket 814 which is crushed against the blowmolded reservoir 802. The force moves the cover 804 from the first and unactuated position to the second and actuated position, as shown in FIGS. 10H-10M.

In various embodiments, the blowmolded reservoir 802 connection to the needle 812 is sealed primarily by piercing the blowmolded reservoir 802. However, the gasket 814 acts as a secondary seal. This is beneficial/desirable for many reasons, including but not limited to, if the needle 812 and blowmolded reservoir 802 do not form a perfect seal, the gasket 814 provides an additional seal.

Upon the cover 804 moving from the first or unactuated position to the second or actuated position, the support feature 806 slides under the mating support feature 818 of the disposable housing assembly 800. This prevents the cover 804 from lifting off of or moving out of relation with the disposable housing assembly 800. Also, the catch feature 808 slides under the mating catch feature 816 on the disposable housing assembly 800 and the cover 804 is locked into place.

In various embodiments, the disposable housing assembly 800 also includes a support block 820 for the blowmolded reservoir 802. The support block 820 supports the position of the blowmolded reservoir 802 so that the blowmolded reservoir 802 maintains its position and does not move when the cover 804 slides and the needle 812 pierces the blowmolded reservoir 802.

With respect to the needle 812, in various embodiments, when the cover 804 slides in the second or actuated position, the needle 812 shape changes slightly as it extends and/or unbends. The cover 804 sliding also provides a force needed for the needle 812 to pierce the reservoir.

Figure 11A:
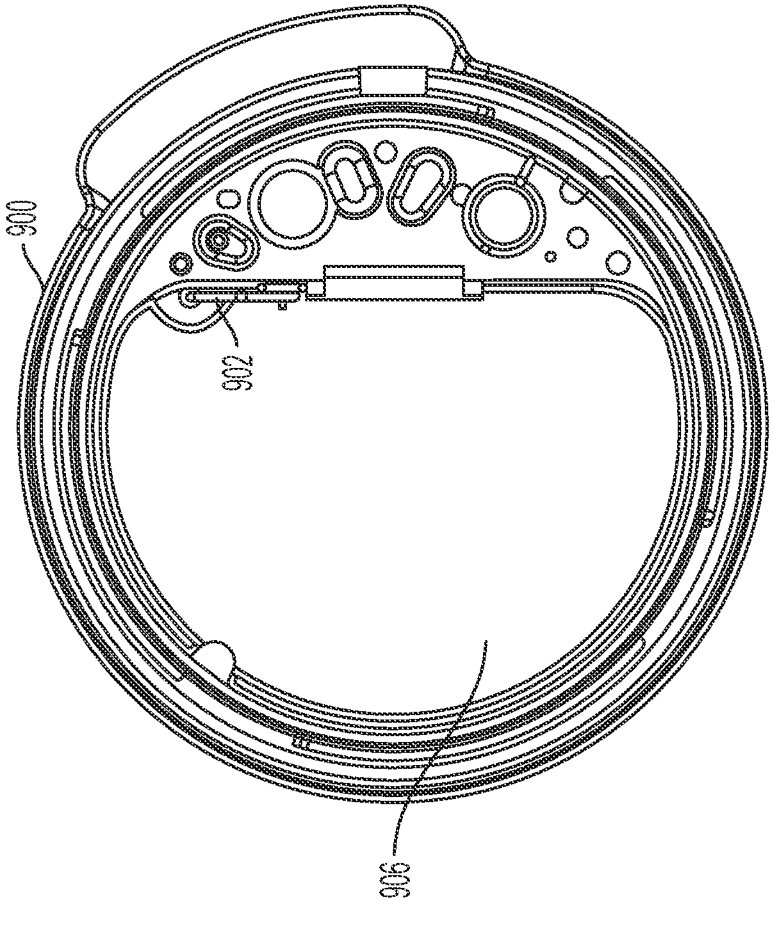
FIGS. 11A-11C are various views of one embodiment of a disposable housing assembly.
Figure 11B:
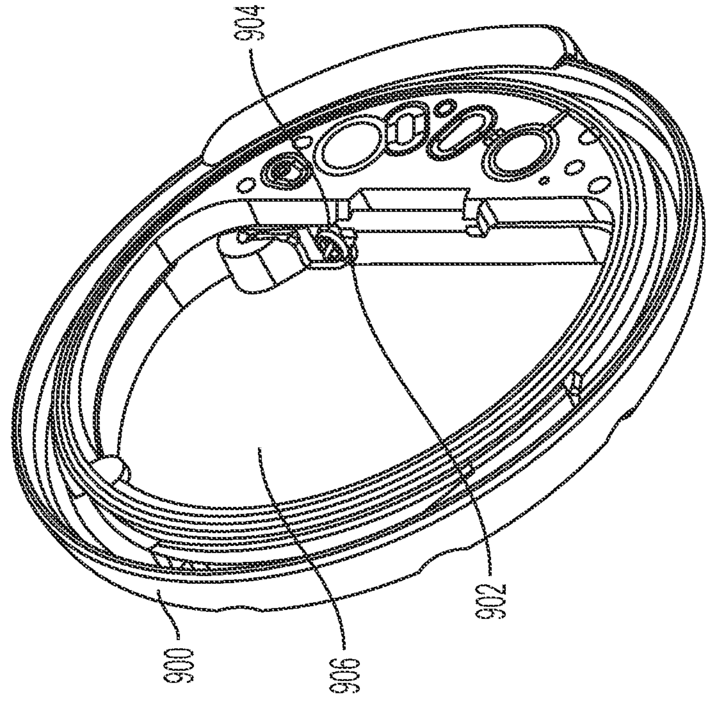
Figure 11C:
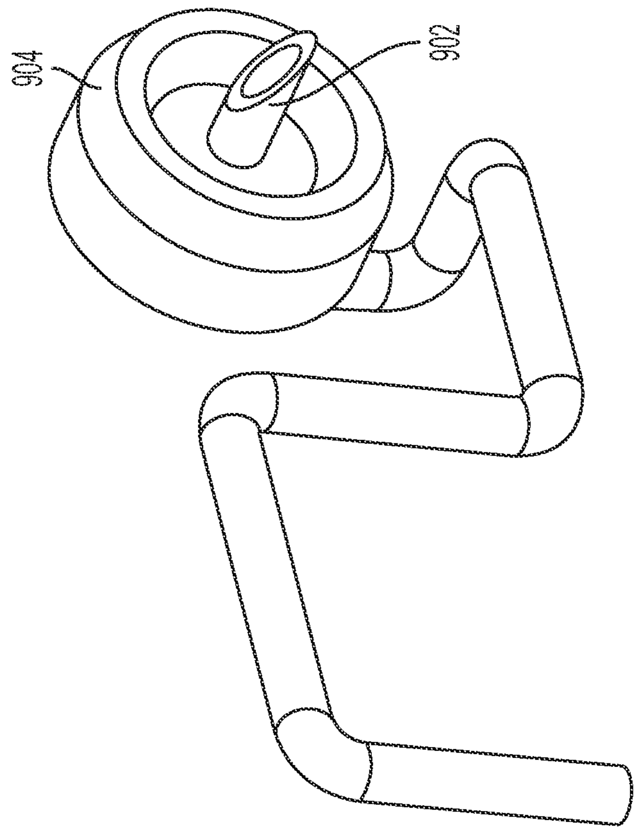
Figure 12A:
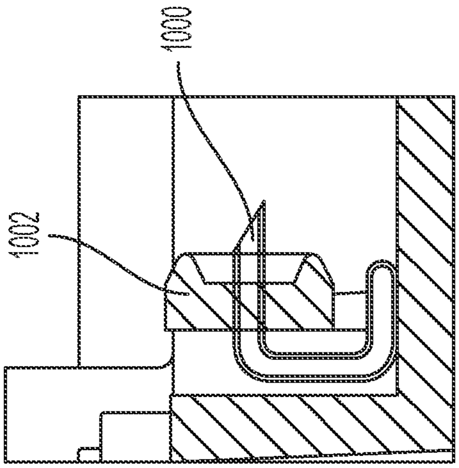
FIGS. 12A-12D are various views of one embodiment of a needle apparatus.
Figure 12B:
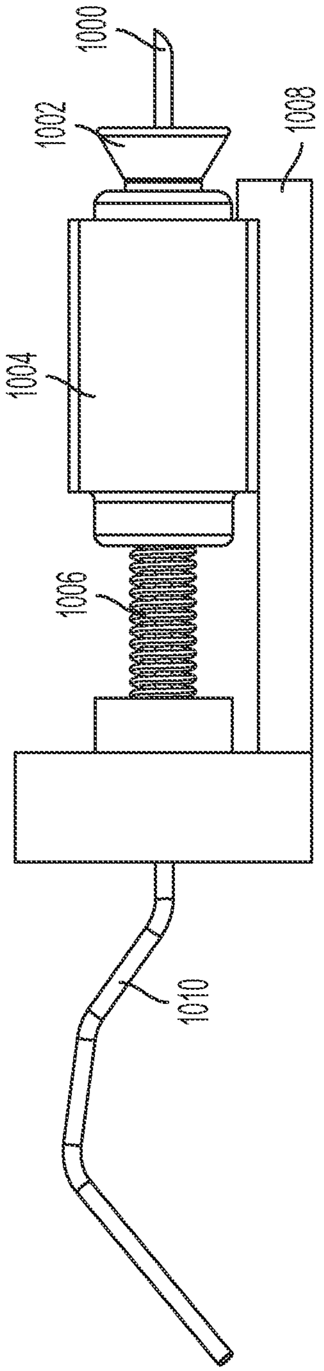
Figure 12C:
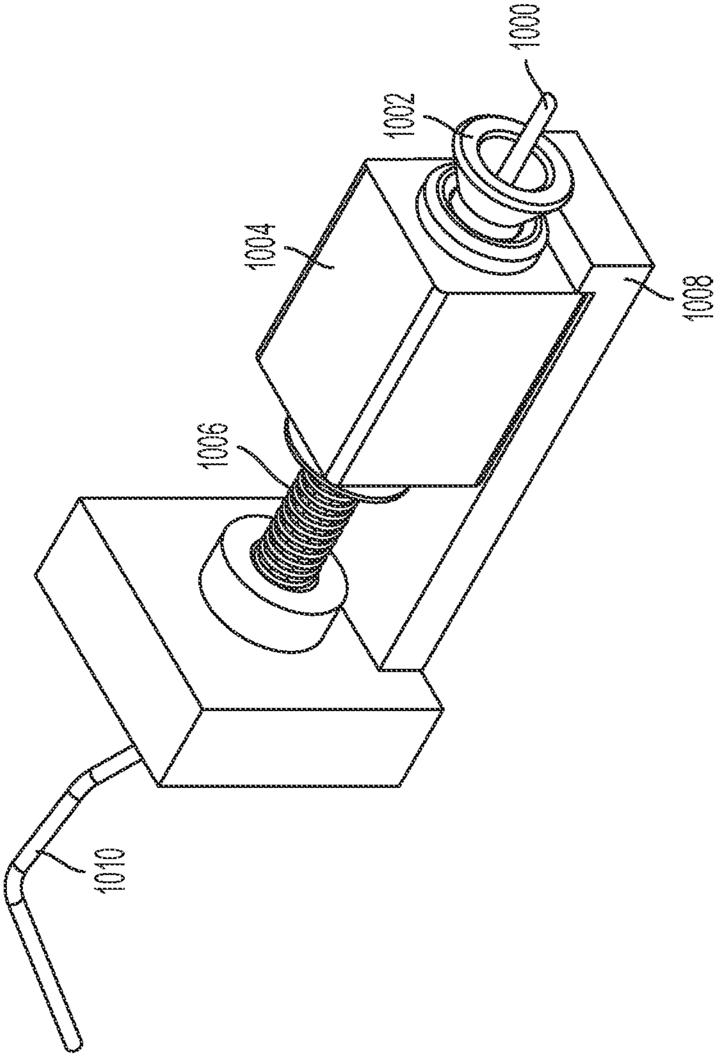
Figure 12D:
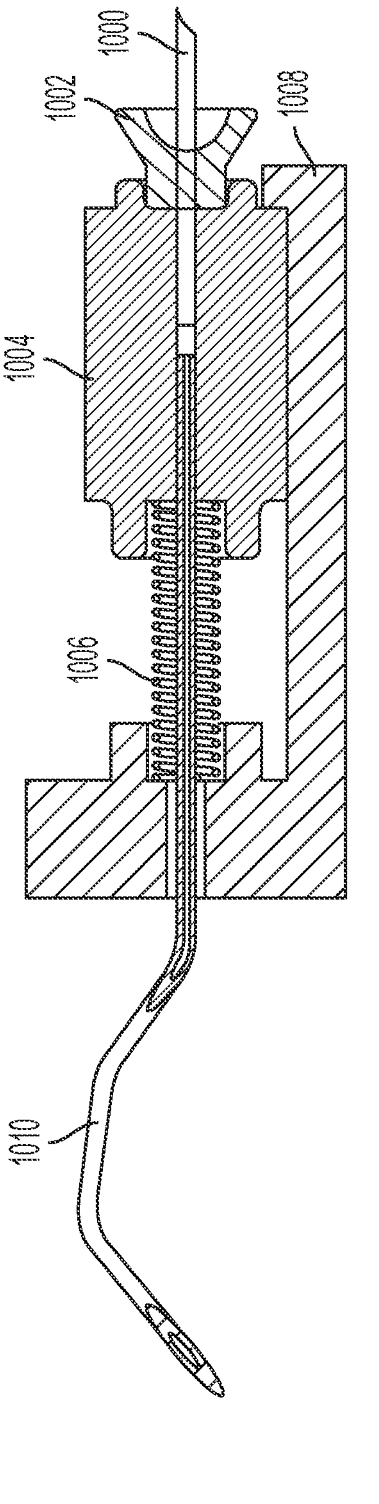

Referring now also to FIGS. 11A-11C, in some embodiments, the needle 902 may be any shape or size and may, in some embodiments, include a gasket 904. The gasket 904, may be as shown in FIGS. 11A-11C, wherein the needle 902 end is outside the gasket 904 in the first or unactuated position. However, in various embodiments, the needle 902 end may be inside the gasket 904 in the first or unactuated position. In various embodiments, a blowmolded reservoir (not shown in FIGS. 11A-11C) may be inserted into the reservoir receiving area 906 of the disposable housing assembly 900. A cover (not shown) may be attached to the disposable housing assembly 900 and force exerted onto the cover may cause the blowmolded reservoir and needle 902 to come into contact and the needle 902 to pierce the blowmolded reservoir. As discussed above, in various embodiments, the needle 902 and blowmolded reservoir may form a seal, however, a gasket 904 may be included in some embodiments to serve as a backup or secondary seal.

Although the needle is shaped/configured and sized as shown in these various figures, other shapes/configurations and sizes may be used in any of the various embodiments described herein. Thus, in various embodiments, the needle may have any shape/configuration including one or more turns, bends, curves, etc. Further, although the gasket is shown herein, other shapes and/or sizes of gaskets or other types of seals may be used. Additionally, in some embodiments, more than one gasket and/or seal may be used.

Referring now also to FIGS. 12A-12D, in various embodiments, rather than a cover, other mechanisms may be used to force a needle into the blowmolded reservoir (not shown). For example, in some embodiments, a needle 1000, which includes at least one sharp end, and, in some embodiments, may be in close relation to a gasket 1002, may be held in place by a shuttle 1004. In various embodiments, the shuttle 1004 is connected to a spring 1006 and contained by a latch feature 1008. When the latch feature 1008 is displaced, the spring 1006, which is adjacent to and, in some embodiments, attached to, the shuttle 1004, propels the shuttle 1004 along an axis and the needle 1000 through the blowmolded reservoir (not shown). Although one configuration is shown in FIGS. 12A-12D, in various embodiments, the shuttle, spring, needle shape and/or latch feature may be shaped and/or configured differently. In some embodiments, the latch feature 1008 may be displaced by a cover, trigger, or any other mechanism that may displace the latch feature 1008. In various embodiments, the fluid path 1010 connects the contents of the blowmolded reservoir to an infusion set, which, in various embodiments, may be any infusion set and in some embodiments, may include any entry into a user for delivery of fluid contained within a blowmolded reservoir. In some embodiments, the fluid path 1010 may be incorporated into a disposable housing assembly and may be a separate tubing or molded directly into the disposable housing assembly.

As discussed above, the gasket 1002 may contain the sharp end of the needle 1000 or the sharp end of the needle 1000 may protrude from the gasket 1002 in the first or unactuated state. In various embodiments, the gasket 1002 provides a seal and/or secondary and/or backup seal for the seal between the needle 1000 and the blowmolded reservoir.

Figure 13A:
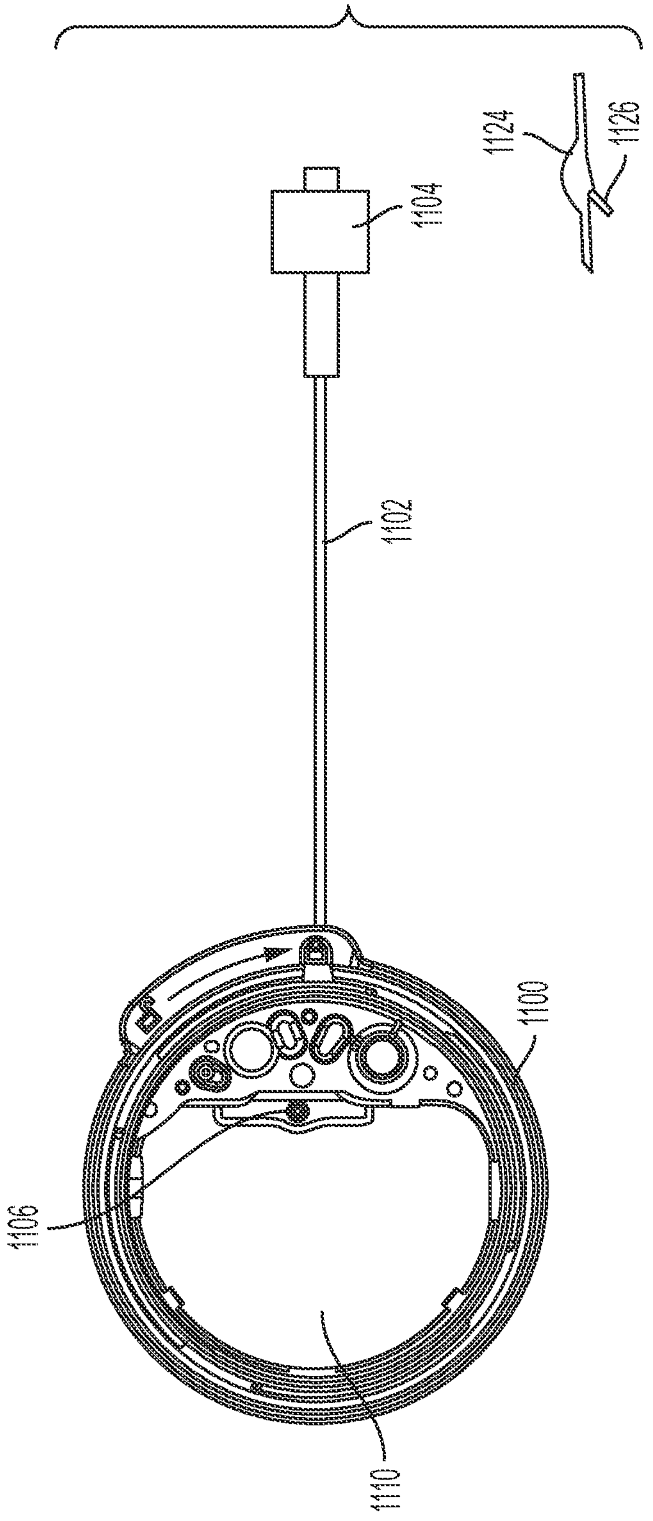
FIGS. 13A-14 are various views of one embodiment of a disposable housing assembly.
Figure 13B:
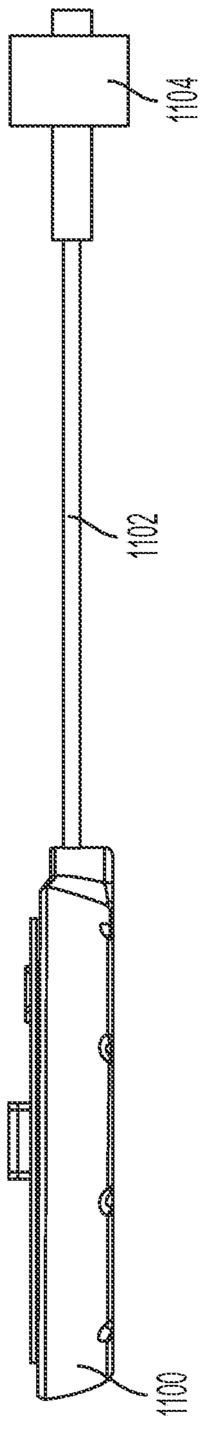
Figure 13C:
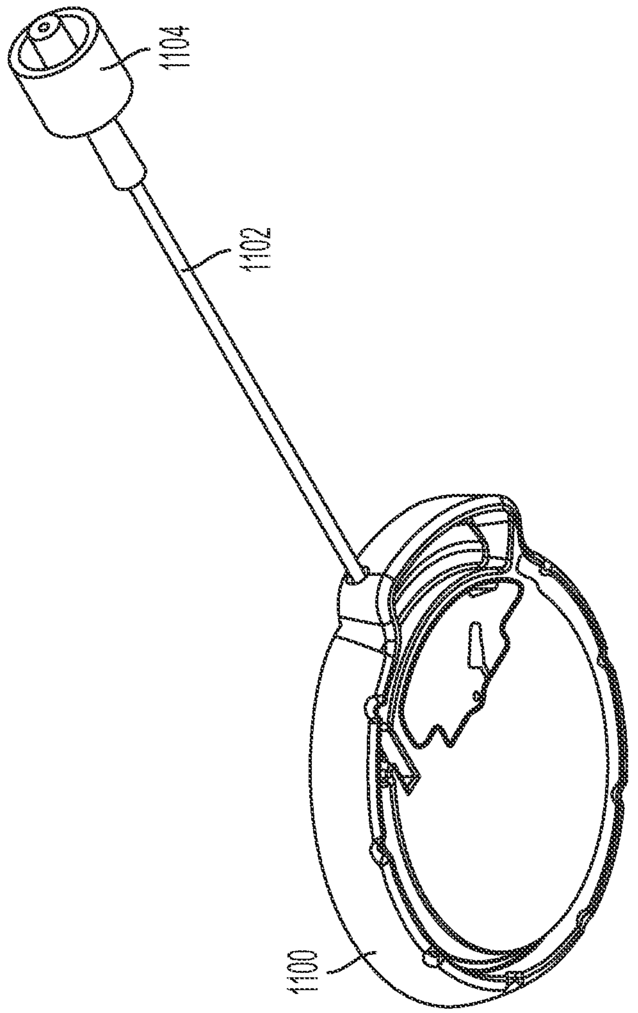
Figure 13D:
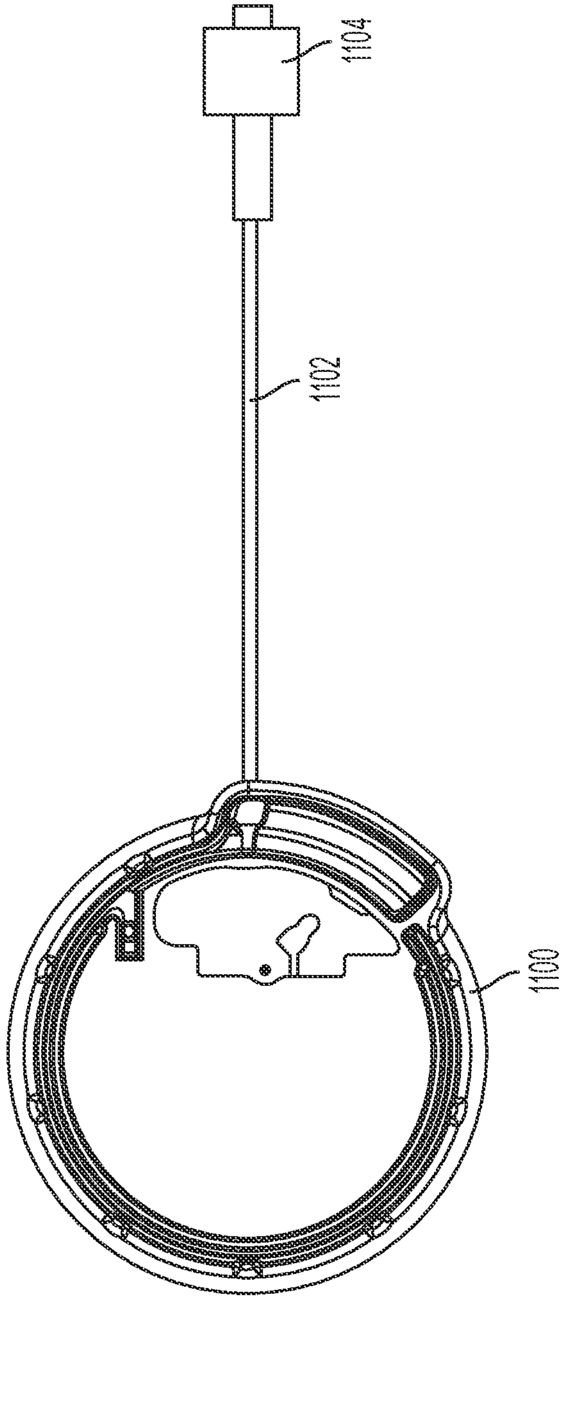
Figure 13E:
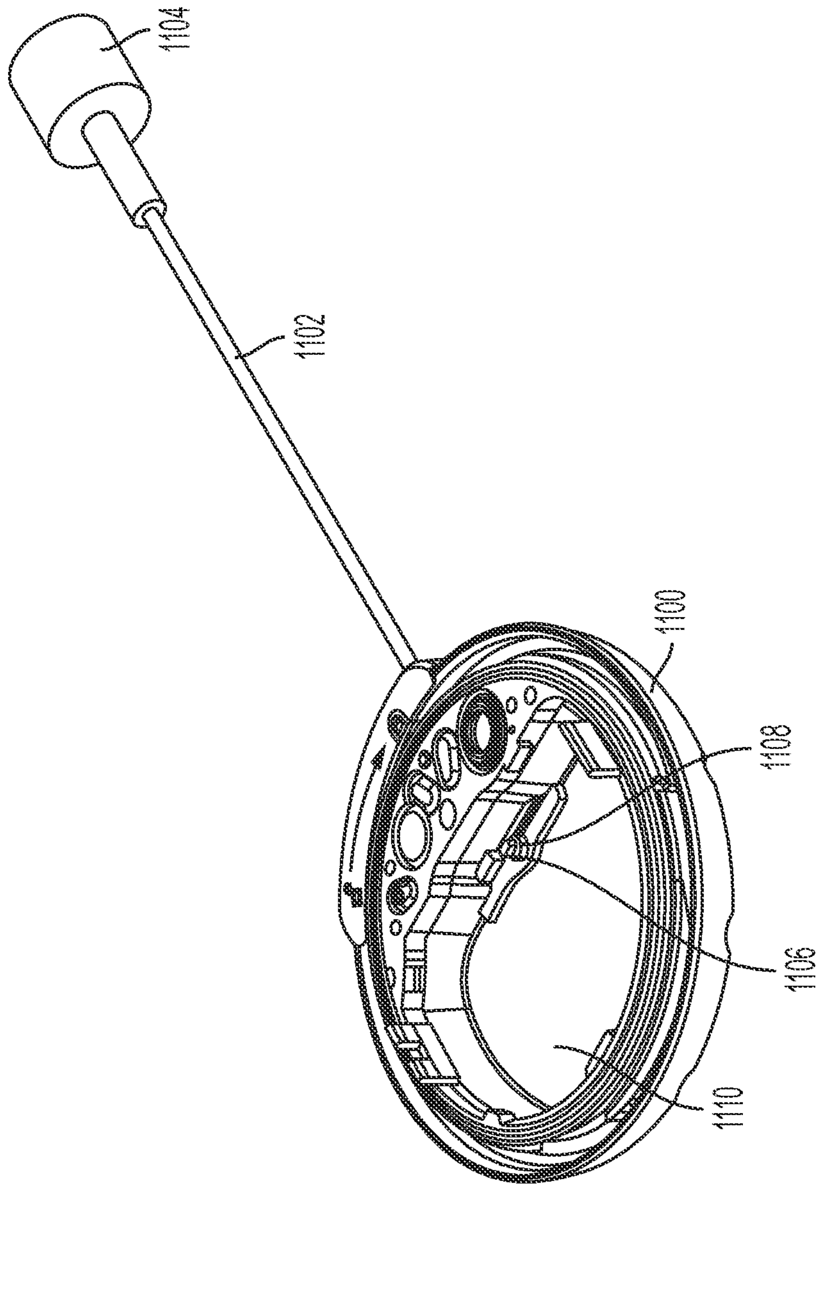
Figure 14:
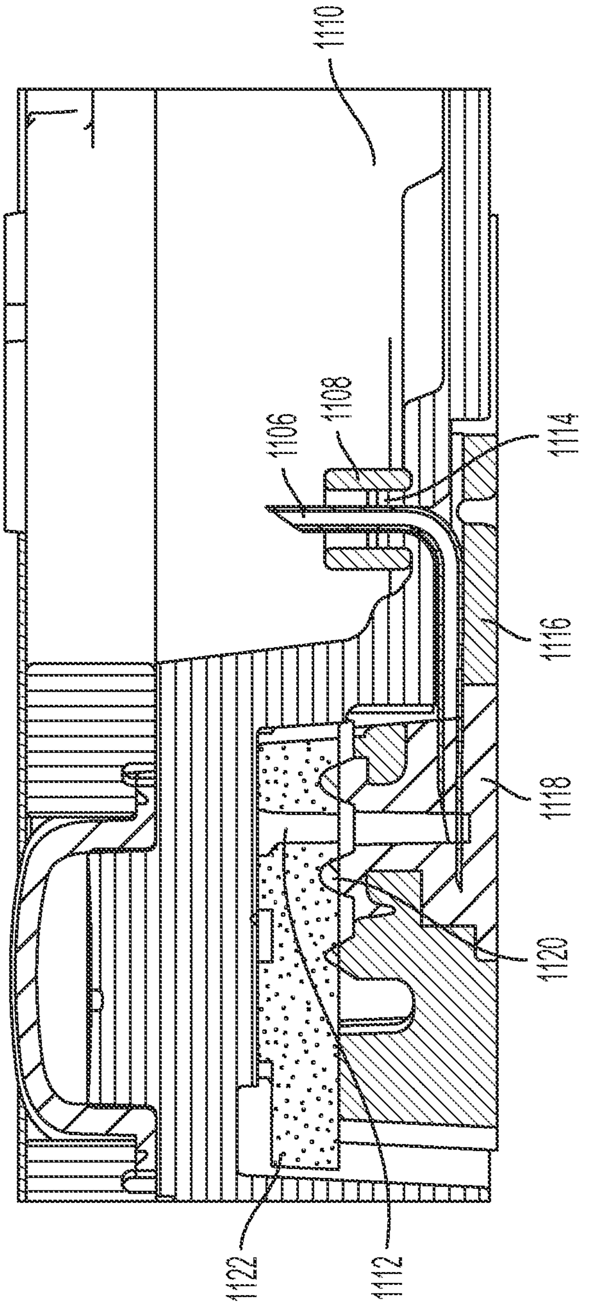
Figure 15A:
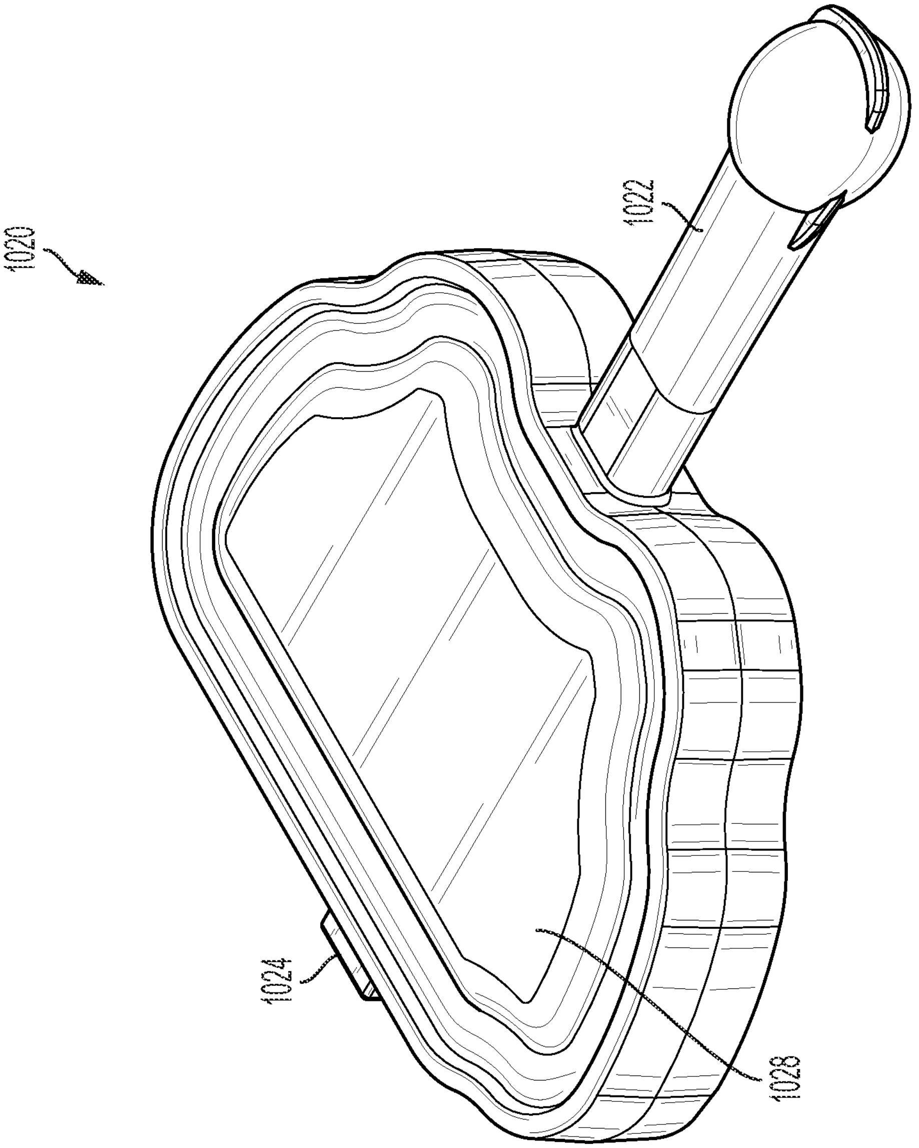
FIGS. 15A-15G are various views of one embodiment of a blowmolded reservoir.
Figure 15B:
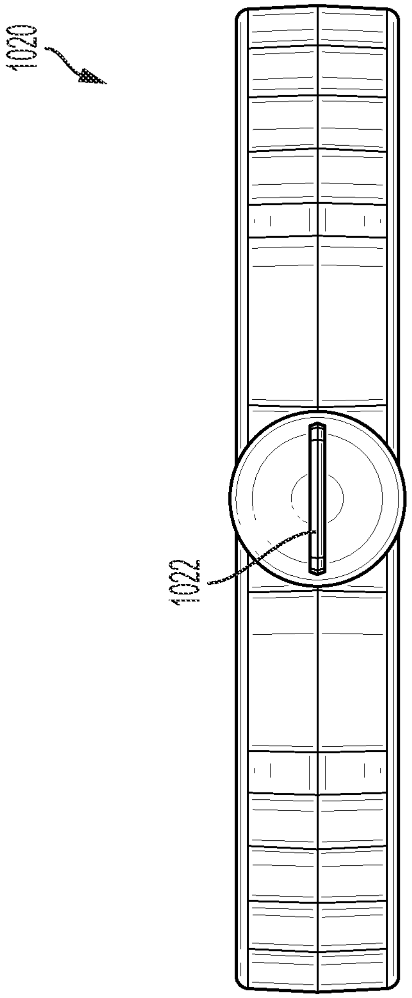
Figure 15C:
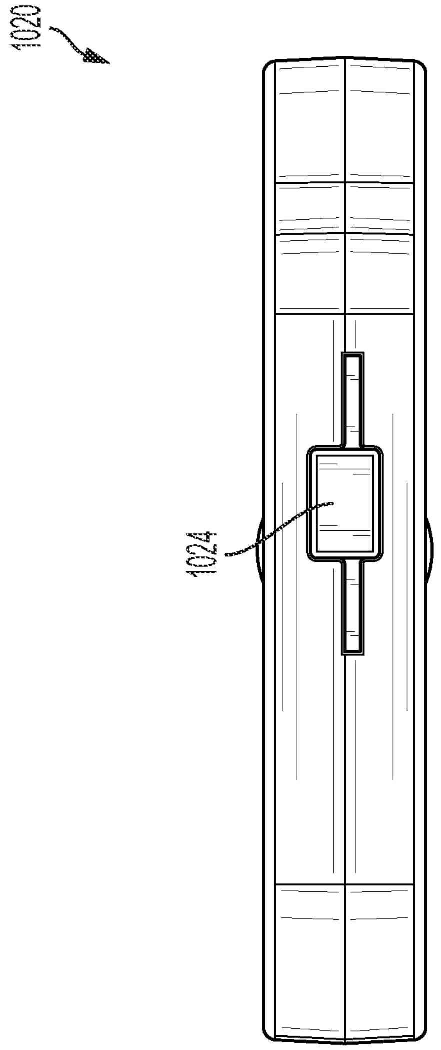
Figure 15D:
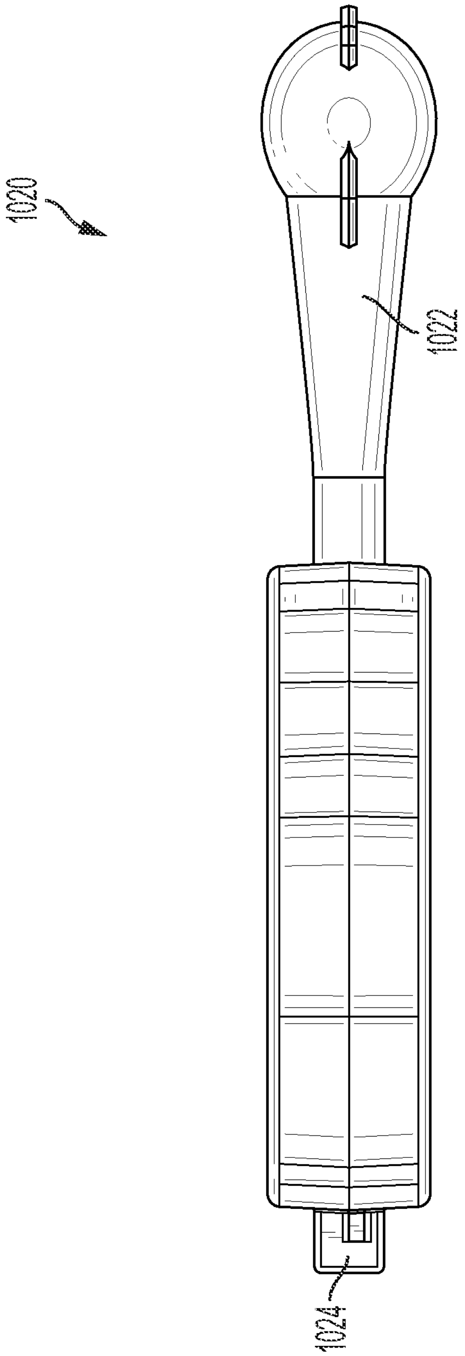
Figure 15E:
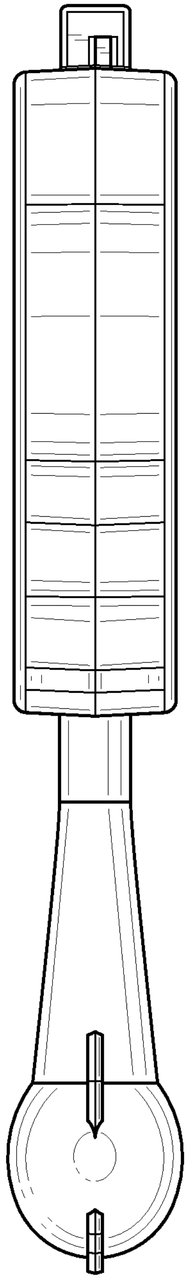
Figure 15F:
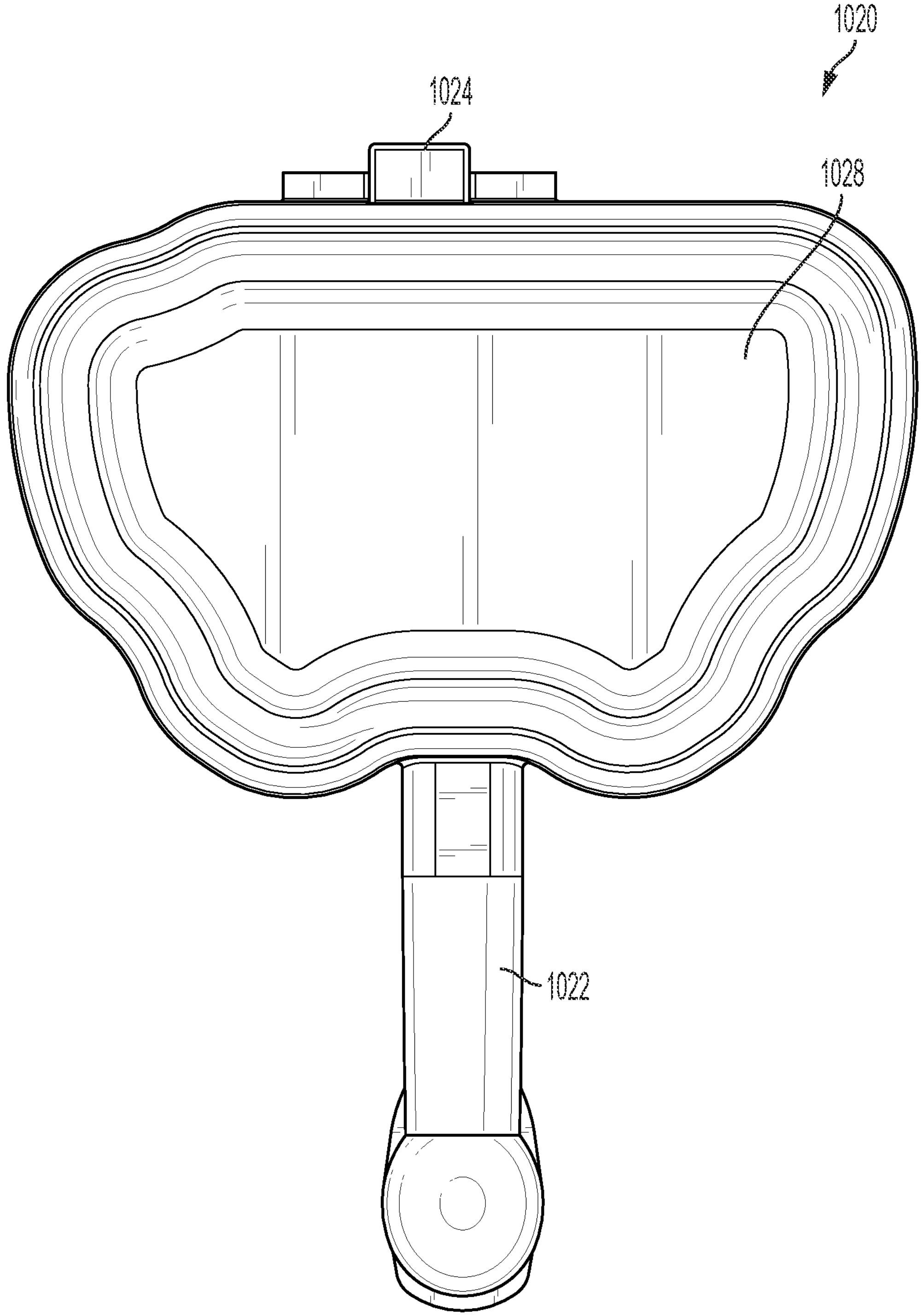
Figure 15G:
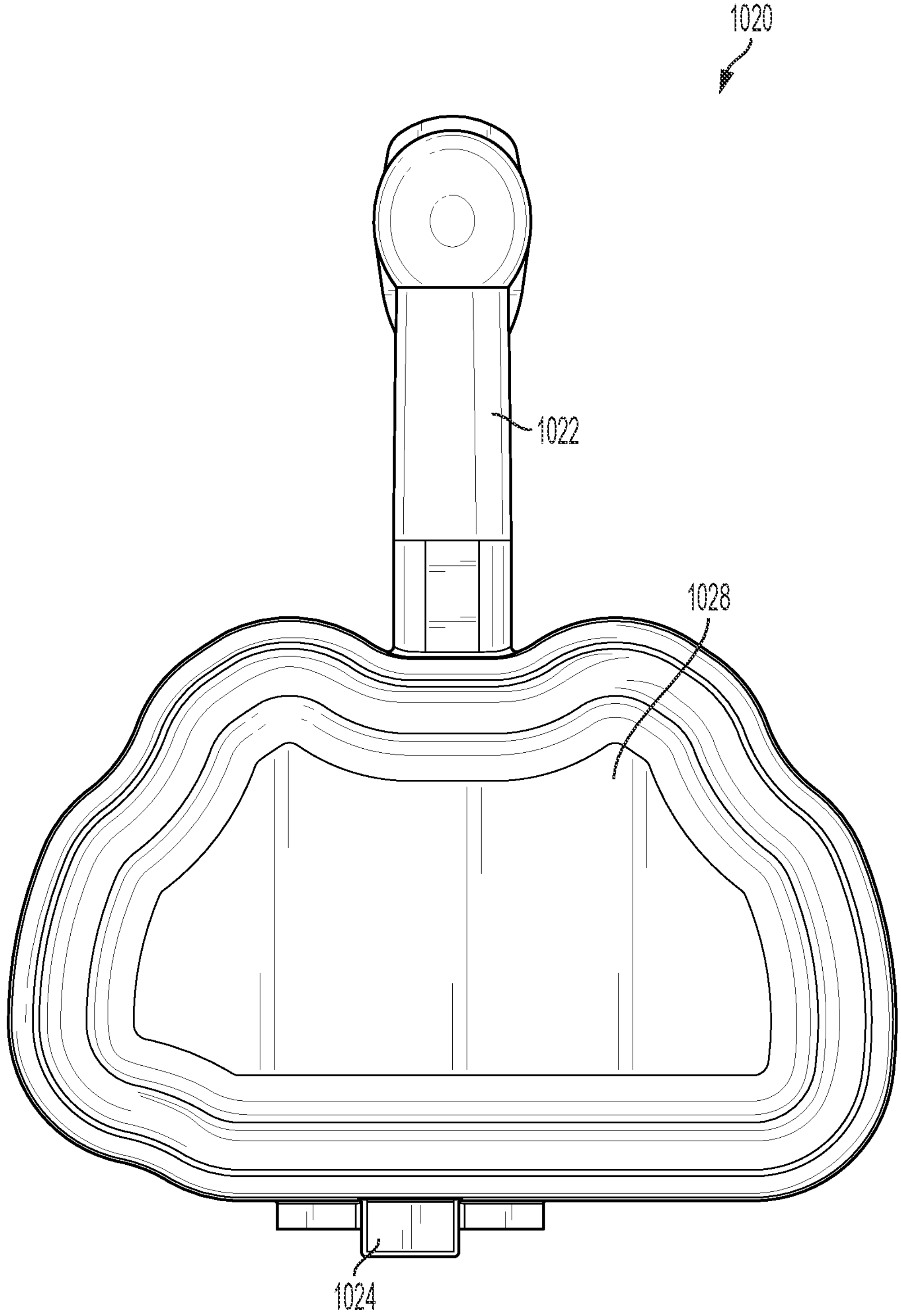
Figure 16A:
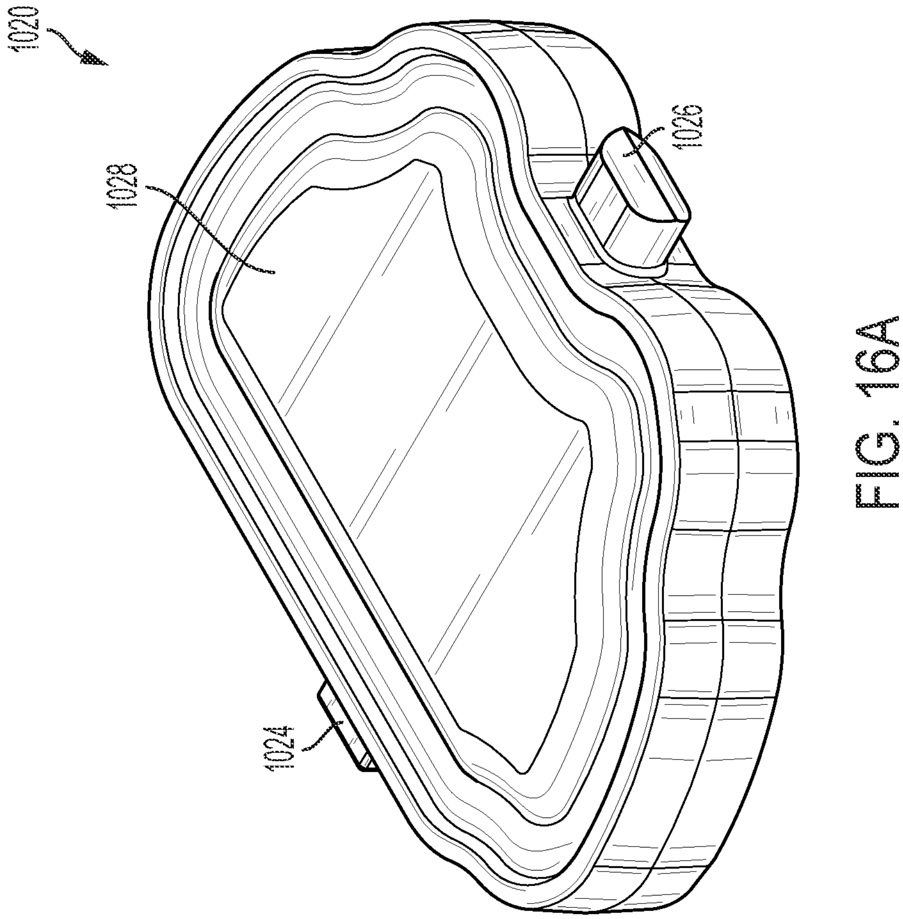
FIGS. 16A-16G are various views of one embodiment of a blowmolded reservoir.
Figure 16B:
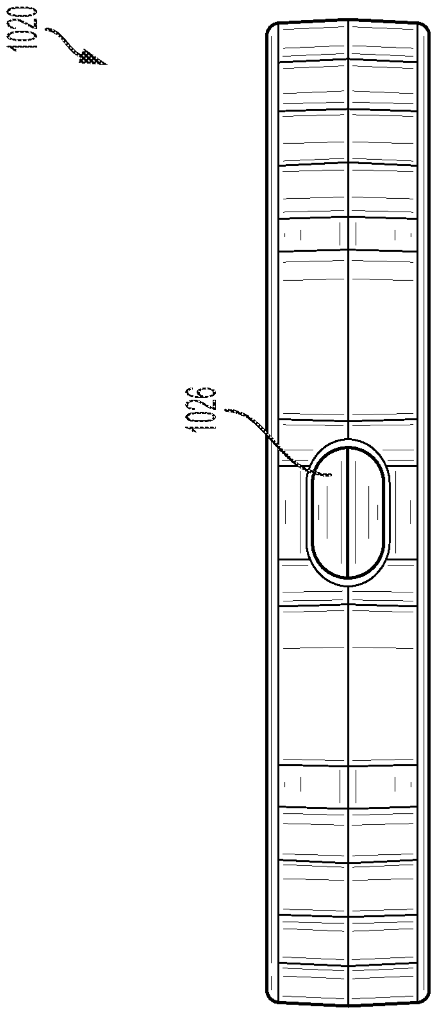
Figure 16C:
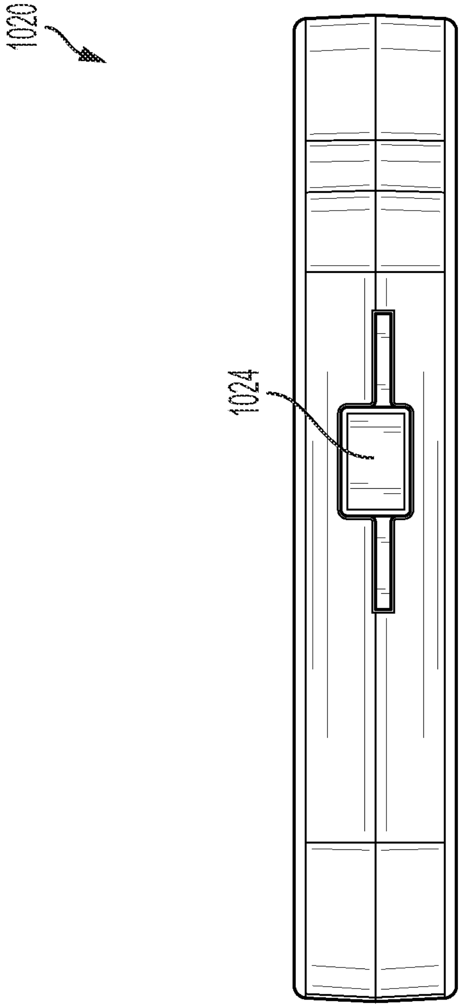
Figure 16D:
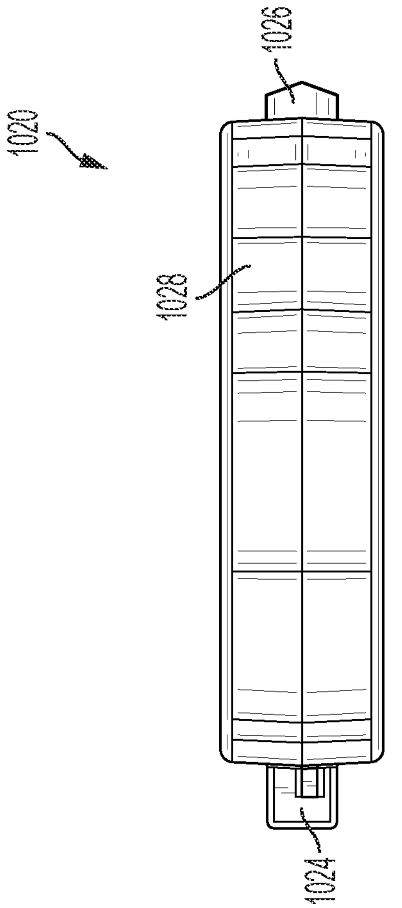
Figure 16E:
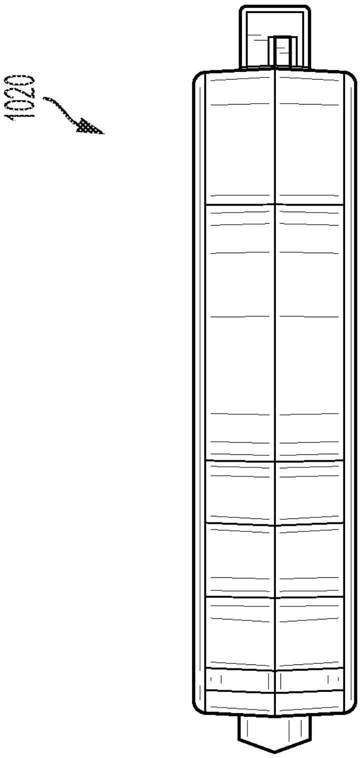
Figure 16F:
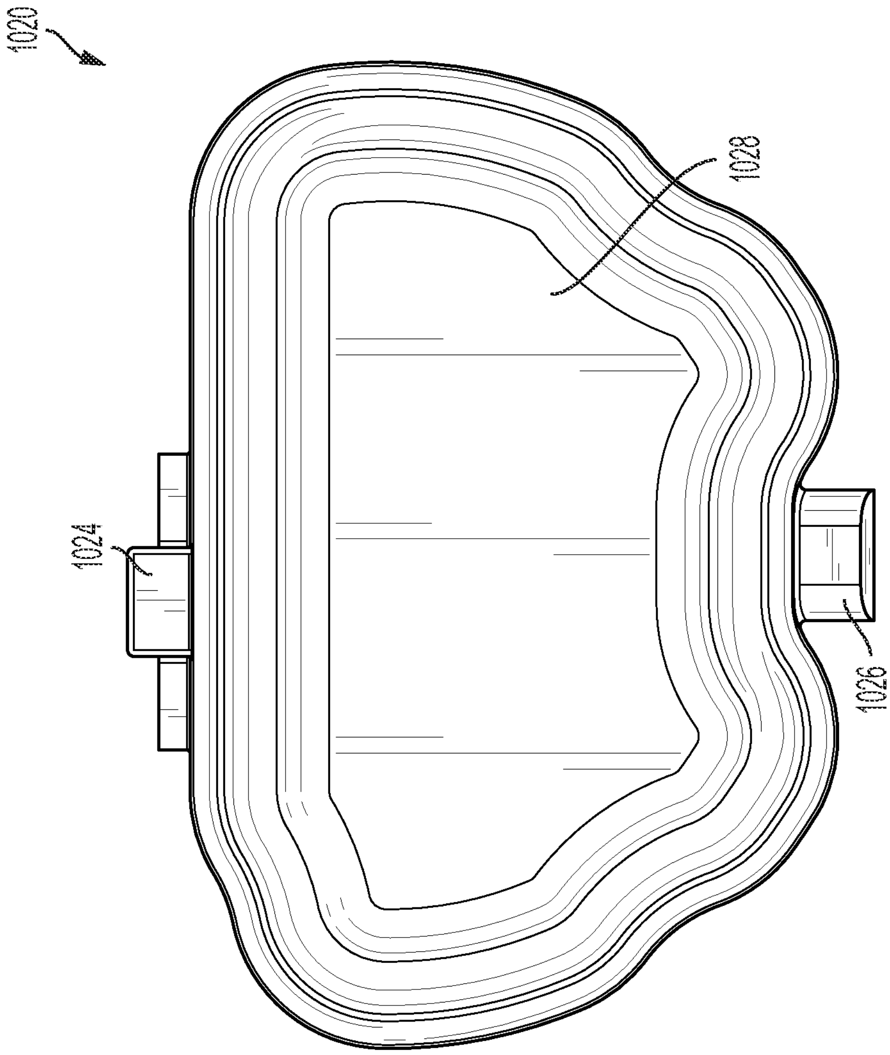
Figure 16G:
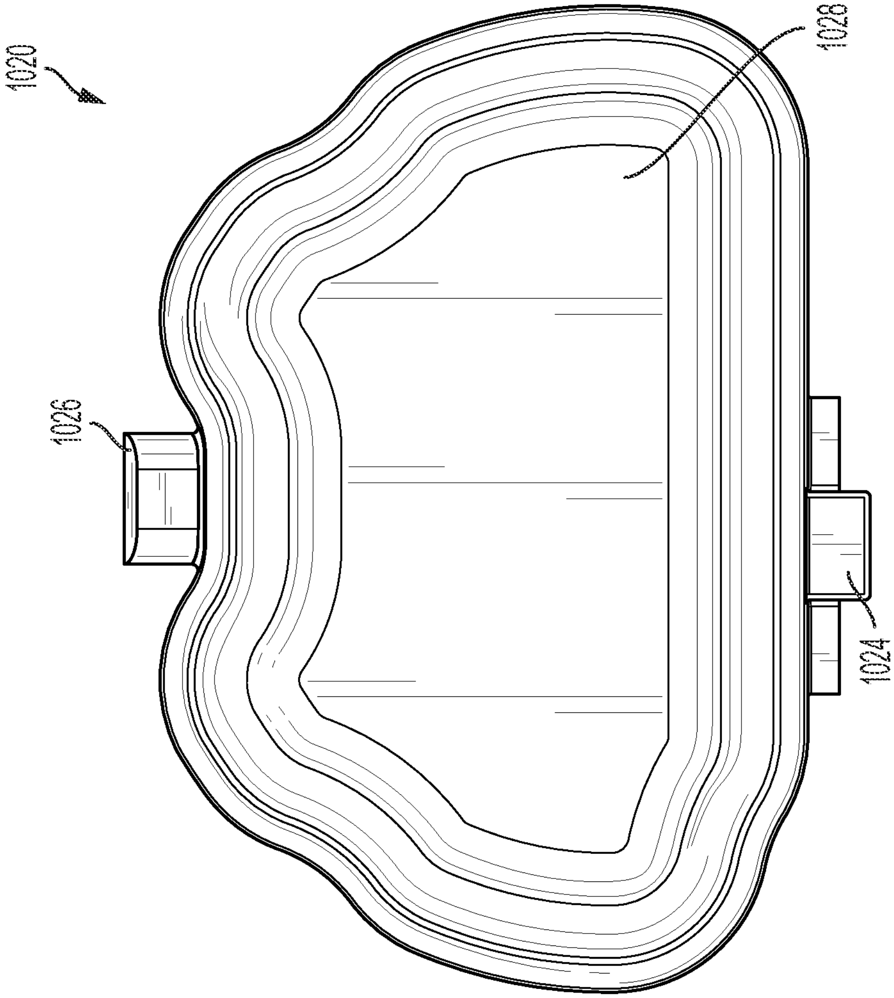
Figure 17A:
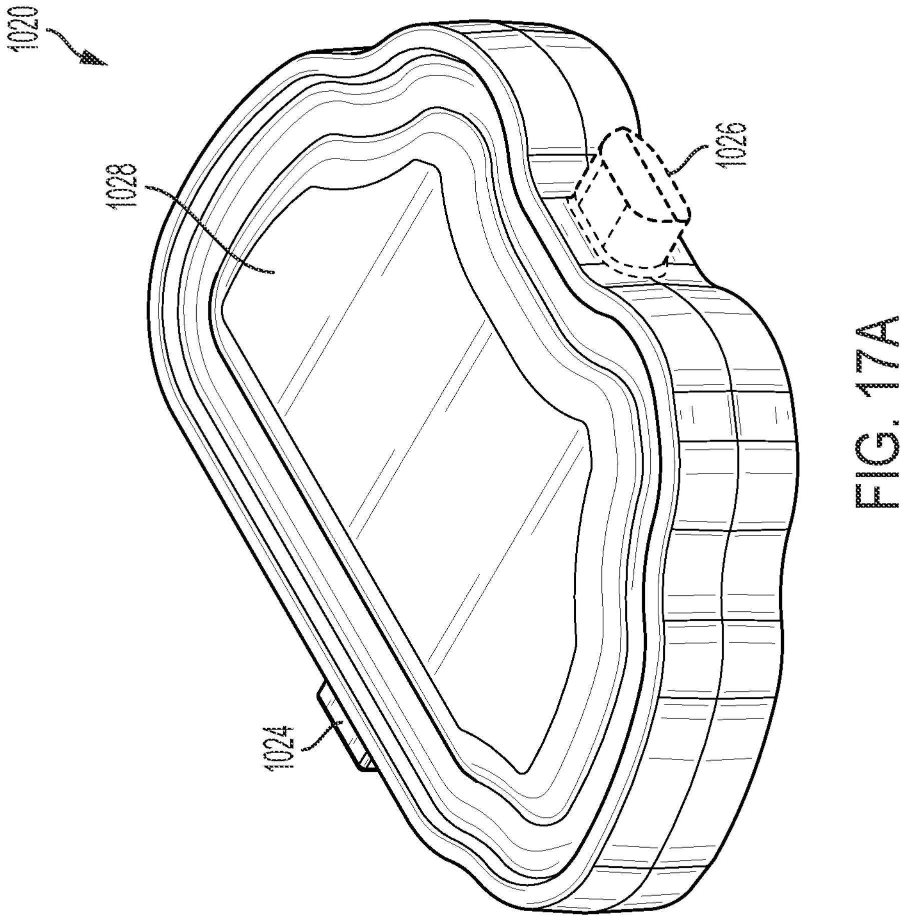
FIGS. 17A-17G are various views of one embodiment of a blowmolded reservoir.
Figure 17B:
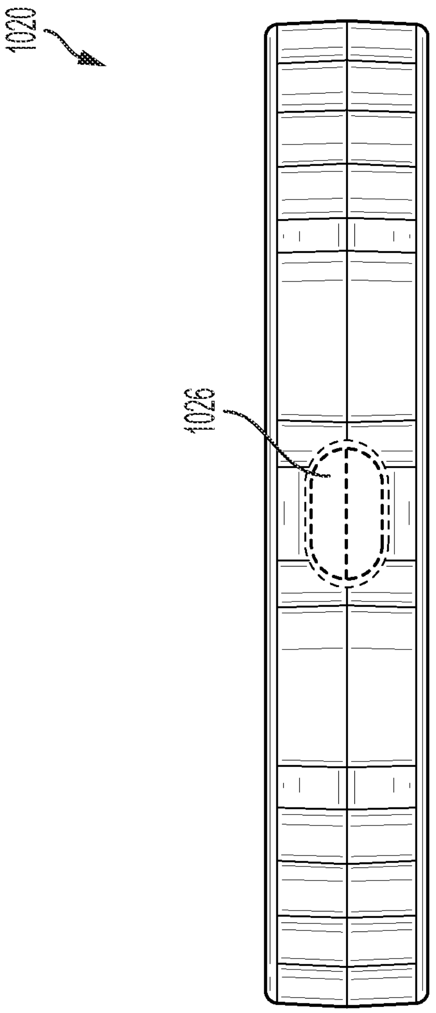
Figure 17C:
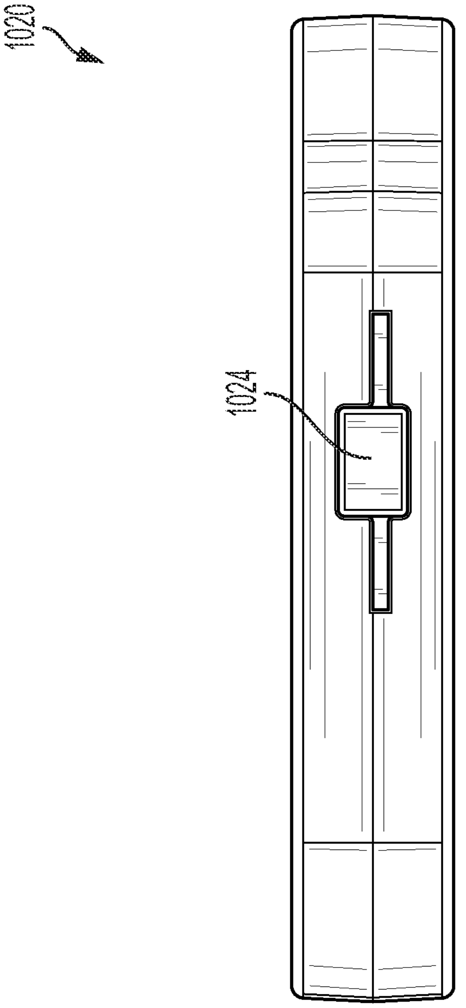
Figure 17D:
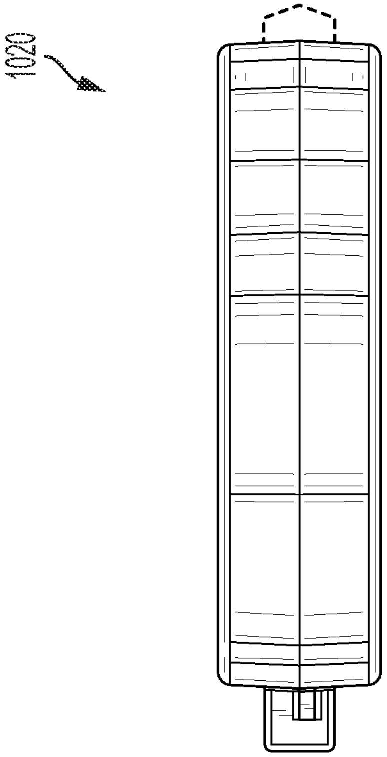
Figure 17E:
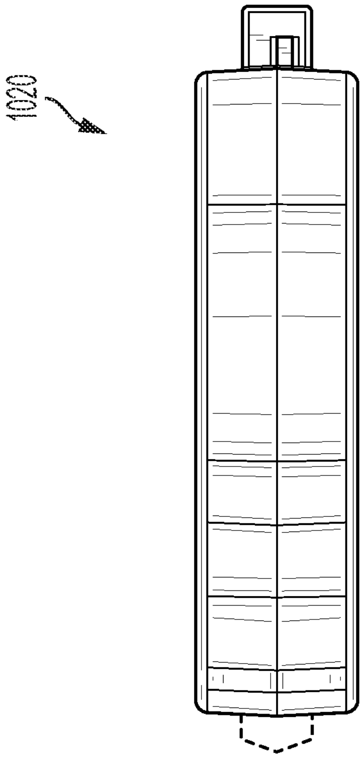
Figure 17F:
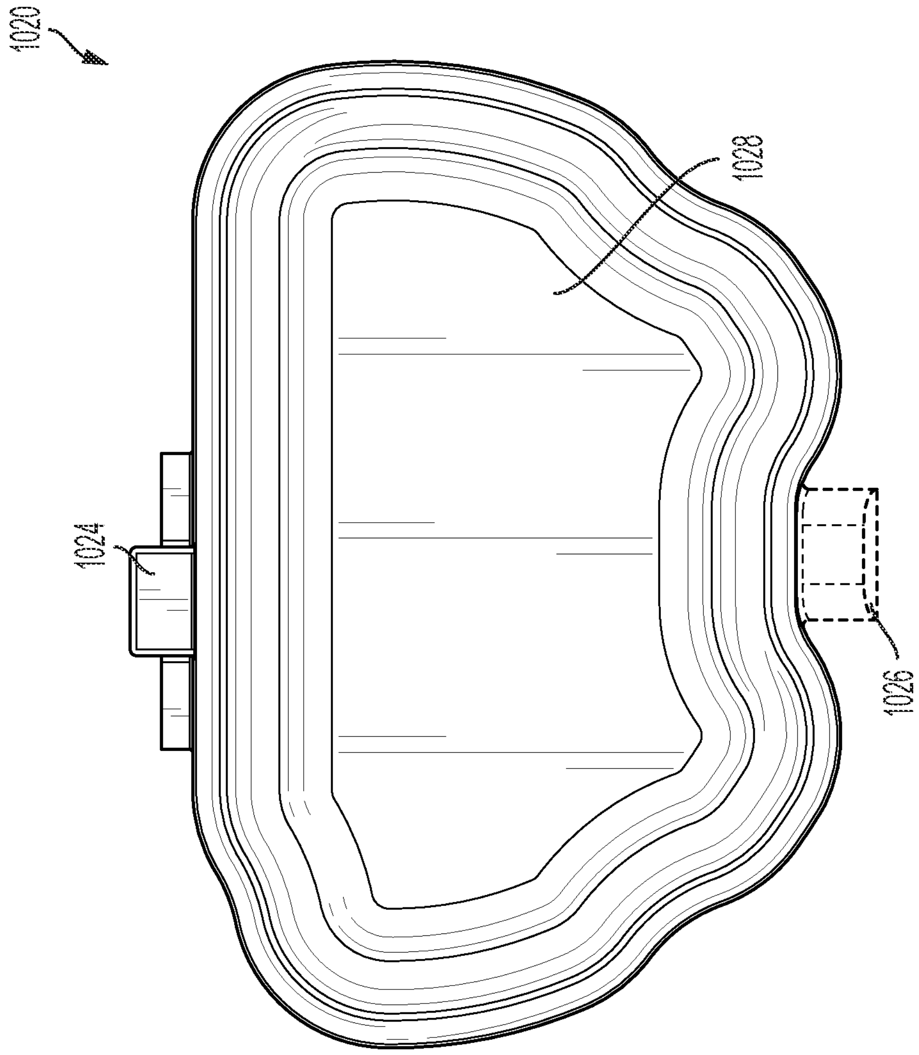
Figure 17G:
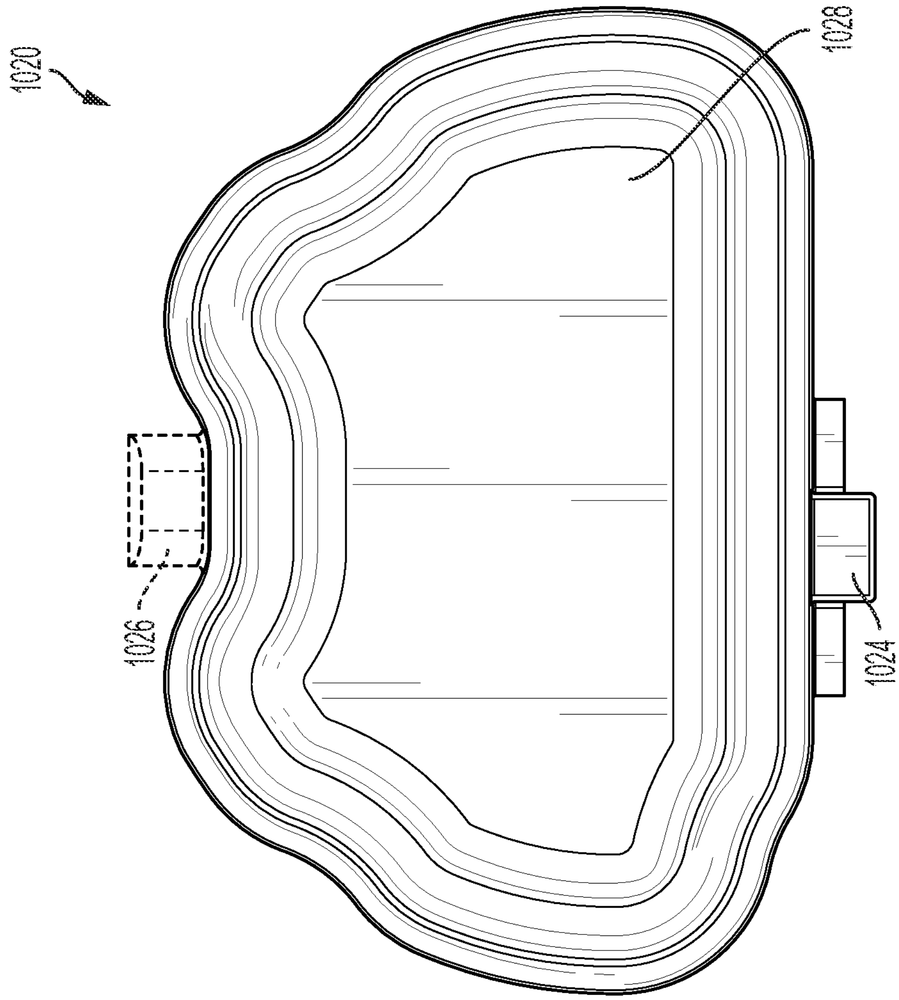

Referring now also to FIGS. 13A-14, another embodiment of a disposable housing assembly 1100, which may include a length of tubing 1102 and a luer connector 1104 (which, although not shown in various embodiments, may be attached to an infusion set 1124 including a cannula 1126, a representation of which is shown in FIG. 13A), may be used with any of the above-described embodiments of various covers and/or blowmolded reservoirs. As shown in FIGS. 13A-14, the disposable housing assembly 1100 is depicted without any covers. However, in various embodiments, the disposable housing assembly 1100 includes a cover including, but not limited to, any of the various covers described herein. In various embodiments, the disposable housing assembly 1100 may or may not include the tubing 1102 and or luer connector 1104.

Still referring to FIGS. 13A-14, the disposable housing assembly 1100 includes a reservoir cavity 1110 configured to receive a blowmolded reservoir. In various embodiments, the shape of the needle 1106 may be as shown in FIGS. 13A, 13E and 14, or may be various other shapes and sizes. In the embodiments shown in FIGS. 13A, 13E and 14, the needle include a single bend and the needle 1106 includes an end that is attached to a gasket 1108. In various embodiments, the end of the needle 1106 attached to the gasket 1108 includes a cylindrical guide 1114. The cylindrical guide 1114 may be beneficial/desirable for many reasons, including but not limited to, the cylindrical guide 1114 contributes to maintaining the needle 1106 in a straight configuration. In some embodiments, the gasket 1108 and needle 1106 may be as shown in FIGS. 13A, 13E and 14, however, in other embodiments, the tip of the needle 1106 may be inside the gasket 1108 in a first or unactuated position (with respect to the cover that is not shown in FIG. 13A, 13E or 14, but various embodiments thereof are described herein). The remaining body of the needle 1106 rests on top of the reservoir, as shown for example in FIG. 10D.

The needle 1106 includes a second end that is press fit into an overmold portion needle cover 1118. A rigid portion needle cover 1116 is also included, both of which maintain the position of the needle 1106. Once the needle 1106 is pressed into the overmolded portion needle cover 1118, the needle 1106 may float. This may be beneficial/desirable for many reasons, including, but not limited to, the end of the needle 1106 that interacts with the reservoir and is located inside the reservoir cavity 1110 may be constrained.

The needle 1106 therefore has a first end that is exposed to the reservoir cavity 1110 and a second end that is exposed to the fluid path 1112. The overmold portion needle cover 1118 includes a fluid seal 1120 wherein this portion of the overmold portion needle cover 1118 creates an o-ring face seal where this portion of the material is crushed against the fluid cover 1122 of the disposable housing assembly 1100. The rigid portion needle cover 1116 in various embodiments is ultrasonically welded to attach to the fluid cover 1122 portion of the disposable housing assembly 1100 to a bottom portion of the disposable housing assembly 1100.

The cover moves from the first or unactuated position to the second or actuated position with the application of force on the cover. In the second or actuated position, the cover has moved and the force of the cover pushes the needle 1106 such that it pierces through the reservoir. The force exerted on the cover is also translated to the gasket 1108 which is crushed against the blowmolded reservoir. The force moves the cover from the first and unactuated position to the second and actuated position.

In various embodiments, the blowmolded reservoir connection to the needle 1106 is sealed primarily by piercing the blowmolded reservoir. However, the gasket 1108 acts as a secondary seal. This is beneficial/desirable for many reasons, including but not limited to, if the needle 1106 and blowmolded reservoir do not form a perfect seal, the gasket 1108 provides an additional seal. Still referring to FIGS. 13A, 13E, and 14, in some embodiments, the needle 1106 may be any shape or size and may, in some embodiments, include a gasket 1108. The gasket 1108, may be as shown in FIGS. 13A, 13E, and 14, wherein the needle 1106 end is outside the gasket 1108 in the first or unactuated position. However, in various embodiments, the needle 1106 end may be inside the gasket 1108 in the first or unactuated position. In various embodiments, a blowmolded reservoir (not shown in FIG. 13A, 13E, or 14 but may include any embodiment described herein) may be inserted into the reservoir cavity 1110 of the disposable housing assembly 1100. A cover (not shown) may be attached to the disposable housing assembly 1100 and force exerted onto the cover may cause the blowmolded reservoir and needle 1106 to come into contact and the needle 1106 to pierce the blowmolded reservoir. As discussed above, in various embodiments, the needle 1106 and blowmolded reservoir may form a seal, however, a gasket 1108 may be included in some embodiments to serve as a backup or secondary seal.

In various embodiments of the blowmolded reservoir, the blowmolding process may be designed to cause thinner areas in specific portions of the blowmolded reservoir. Thus, in various embodiments, the wall of the blowmolded reservoir may not be consistent throughout with respect to thickness, rather, the wall thickness may vary in specific locations. In various embodiments, the corner sections of the blowmolded reservoir are thinner than the rest of the reservoir. This may be beneficial/desirable for many reasons, including, but not limited to, increasing the collapsibility of the blowmolded reservoir. In other embodiments, the reservoir may be manufactured with molding equipment and die to include thinner sections. However, in various embodiments, the blowmolded reservoir is manufactured with intentional geometry and variations in wall thickness. Referring now also to FIG. 18, a graphical representation of the various sections of the wall of the embodiment of the blowmolded reservoir shown in FIGS. 15A-17G is shown. The areas 1200, 1202 represent the corners of the reservoir and in various embodiments, the thickness of these areas 1200, 1202 is less than the thickness of the non-corner sections 1204.

In various embodiments, the cover of the disposable housing assembly may include at least one cut-out and or features. In some embodiments, the cut-outs may be any shape or size, and of any plurality (including a single cut-out) and may include a slit or a round cut-out, and may include one or more cut-outs. The features may be any features including, but not limited to, tabs, mating locking features, and/or indicia. In various embodiments, the cut-out(s) and/or feature(s) may also be any of those described in the various references incorporated herein by reference above. Further, in some embodiments, the cover may not include any cut-out(s) and/or feature(s).

Although the needle is shaped/configured and sized as shown in these various figures, other shapes/configurations and sizes may be used in any of the various embodiments described herein. Thus, in various embodiments, the needle may have any shape/configuration including one or more turns, bends, curves, etc. Further, although the gasket is shown herein, other shapes and/or sizes of gaskets or other types of seals may be used. Additionally, in some embodiments, more than one gasket and/or seal may be used.

A number of embodiments have been described. Nevertheless, it will be understood that various modifications may be made. Accordingly, other embodiments are within the scope of the following claims.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A disposable housing assembly comprising:

a planar bottom surface for attachment to a user;

a reservoir cavity;

a needle located within the reservoir cavity and parallel to the bottom surface;

a fluid path fluidly connected to the needle; and a cover, wherein the cover is hinged and configured to move from a first position to a second position in a hinged movement, and the cover comprises at least one ear configured to interact with and pull a reservoir towards the needle such that the needle pierces a seal located within the reservoir when the cover is moved from the first position to the second position in the hinged movement;

wherein when the cover is in the first position, the reservoir cavity and the needle are exposed and when the cover is in the second position, the reservoir and needle are not exposed and the reservoir is enclosed inside the disposable housing assembly.

2. The disposable housing assembly of claim 1, wherein the needle comprises a first end and a second end, the first end inside a gasket and the second end inside an overmolded portion needle cover.

3. The disposable housing assembly of claim 1, further comprising a rigid portion needle cover.

4. The disposable housing assembly of claim 1, wherein the needle comprises a first end and a second end, wherein the first end is exposed to the reservoir cavity and the second end is exposed to the fluid path.

5. The disposable housing assembly of claim 1, further comprising a cylindrical guide located about a gasket, wherein the needle comprises a first end and a second end, the first end inside the gasket.

6. The disposable housing assembly of claim 1, wherein the needle comprises a bend.

7. The disposable housing assembly of claim 1, further comprising a gasket, wherein the needle is located in the gasket.

8. The disposable housing assembly of claim 1, further comprising an exit fluidly connected to the fluid path.

9. The disposable housing assembly of claim 8, further comprising a predetermined length of tubing attached to the fluid path.

10. The disposable housing assembly of claim 1, wherein the cover further comprises at least one catch feature.

11. The disposable housing assembly of claim 10, further comprising a mating feature engageable to the at least one catch feature to hold the cover in the second position.

12. The disposable housing assembly of claim 1, wherein the reservoir cavity comprises:

the reservoir; and a fluid, wherein the fluid is maintained in the reservoir.

13. The disposable housing assembly of claim 12, further comprising a luer of an infusion set attached to the fluid path.

14. The disposable housing assembly of claim 13, further comprising a cannula attached to the luer.

15. The disposable housing assembly of claim 1, wherein the cover comprises at least one catch feature.

16. The disposable housing assembly of claim 15, wherein the catch feature is engaged in the second position.

17. The disposable housing assembly of claim 1, wherein the cover comprises a plurality of catch features.

18. The disposable housing assembly of claim 1, wherein the cover comprises a needle holder feature.

19. The disposable housing assembly of claim 1, wherein the cover comprises a support feature.

20. The disposable housing assembly of claim 1, wherein the needle comprises a first end and a second end, the first end attached to a gasket.

21. A disposable housing assembly comprising:
- a planar bottom surface for attachment to a user;
- a reservoir cavity;
- a needle located within the reservoir cavity and parallel to the bottom surface;
- a fluid path fluidly connected to the needle; and
- a hinging door, wherein the hinging door is configured to move from a first position to a second position in a hinged movement, and the hinging door comprises at least one ear configured to interact with and pull a reservoir towards the needle such that the needle pierces a seal located within the reservoir when the hinging door is moved from the first position to the second position in the hinged movement;
- wherein when the hinging door is in the first position, the reservoir cavity and needle are exposed and when the hinging door is in the second position, the reservoir and needle are not exposed and the reservoir is enclosed inside the disposable housing assembly.

22. The disposable housing assembly of claim 21, further comprising a gasket, wherein the needle is located in the gasket.

23. The disposable housing assembly of claim 21, further comprising an exit fluidly connected to the fluid path.

24. The disposable housing assembly of claim 23, further comprising a predetermined length of tubing attached to the exit.

25. The disposable housing assembly of claim 24, further comprising a luer of an infusion set attached to the tubing.

26. The disposable housing assembly of claim 25, further comprising a cannula attached to the luer.

27. The disposable housing assembly of claim 21, wherein the hinging door comprises at least one catch feature.

28. The disposable housing assembly of claim 21, wherein the hinging door comprises at least one catch feature to hold the hinging door in the second position.

29. The disposable housing assembly of claim 21, wherein the reservoir cavity comprises:
- the reservoir; and
- a fluid maintained in the reservoir.

30. A disposable housing assembly comprising:
- a planar bottom surface for attachment to a user;
- a reservoir cavity;
- a reservoir in the reservoir cavity;
- a needle located within the reservoir cavity and parallel to the bottom surface;
- a fluid path fluidly connected to the needle; and
- a hinging door,
- wherein the hinging door is configured to move from a first position to a second position in a hinged movement, and the hinging door comprises at least one ear configured to interact with and pull the reservoir towards the needle such that the needle pierces a seal located within the reservoir when the hinging door is moved from the first position to the second position in the hinged movement; and
- wherein when the hinging door is in the first position, the reservoir cavity, reservoir and needle are exposed and when the hinging door is in the second position, the reservoir cavity, reservoir and needle are not exposed and the reservoir is enclosed inside the disposable housing assembly.

31. The disposable housing assembly of claim 30, further comprising a latch.

32. The disposable housing assembly of claim 30, further comprising a gasket, wherein the needle is located in the gasket.

33. The disposable housing assembly of claim 30, further comprising an exit fluidly connected to the fluid path.

34. The disposable housing assembly of claim 33, further comprising a predetermined length of tubing attached to the exit.

35. The disposable housing assembly of claim 34, further comprising a luer of an infusion set attached to the tubing.

36. The disposable housing assembly of claim 35, further comprising a cannula attached to the luer.

37. The disposable housing assembly of claim 30, wherein the hinging door comprises at least one catch feature.

38. The disposable housing assembly of claim 30, wherein the hinging door comprises at least one catch feature for holding the hinging door in the second position.

39. The disposable housing assembly of claim 30, further comprising:
- a fluid in the reservoir.

* * * * *